United States Patent
Askarinya et al.

(10) Patent No.: US 9,168,384 B2
(45) Date of Patent: *Oct. 27, 2015

(54) ELECTRODE STRUCTURE FOR IMPLANTABLE MEDICAL DEVICE

(75) Inventors: Mohsen Askarinya, Chandler, AZ (US); Erik J. Herrmann, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1192 days.

This patent is subject to a terminal disclaimer.

(21) Appl. No.: 13/113,720

(22) Filed: May 23, 2011

(65) Prior Publication Data

US 2012/0303105 A1  Nov. 29, 2012

(51) Int. Cl.
*A61N 1/00* (2006.01)
*A61N 1/375* (2006.01)

(52) U.S. Cl.
CPC .............. *A61N 1/375* (2013.01); *A61N 1/3756* (2013.01); *A61N 1/3754* (2013.01); *Y10T 29/49204* (2015.01)

(58) Field of Classification Search
CPC .... A61N 1/375; A61N 1/3752; A61N 1/3754
USPC ...................................... 607/36–37
See application file for complete search history.

(56) References Cited

U.S. PATENT DOCUMENTS

| | | |
|---|---|---|
| 4,254,775 A | 3/1981 | Langer |
| 4,632,798 A | 12/1986 | Eickman et al. |
| 5,117,824 A | 6/1992 | Keimel et al. |
| 5,381,599 A | 1/1995 | Hall |
| 5,461,256 A | 10/1995 | Yamada et al. |
| 5,645,586 A | 7/1997 | Meltzer |
| 5,741,313 A | 4/1998 | Davis et al. |
| 5,873,899 A | 2/1999 | Stutz, Jr. et al. |
| 6,319,208 B1 | 11/2001 | Abita et al. |
| 6,505,077 B1 | 1/2003 | Kast et al. |
| 6,643,552 B2 | 11/2003 | Edell et al. |
| 6,721,602 B2 | 4/2004 | Engmark et al. |
| 7,169,645 B2 | 1/2007 | Bolken et al. |
| 2002/0042634 A1 | 4/2002 | Bardy et al. |
| 2002/0198582 A1* | 12/2002 | Edell et al. .............. 607/116 |
| 2003/0040779 A1 | 2/2003 | Engmark et al. |
| 2003/0144707 A1 | 7/2003 | Ruben et al. |

(Continued)

FOREIGN PATENT DOCUMENTS

WO  2004041072 A2  5/2004

OTHER PUBLICATIONS

Office Action from co-pending U.S. Appl. No. 13/113,685 dated Apr. 1, 2013 (10 pages).

(Continued)

*Primary Examiner* — Christopher Koharski
*Assistant Examiner* — Roland Dinga
(74) *Attorney, Agent, or Firm* — Evans M. Mburu

(57) ABSTRACT

An IMD may include a liquid crystal polymer (LCP) outer housing defining an outer surface of the IMD, an electrical feedthrough extending through the LCP outer housing to the outer surface, and an electrode structure disposed on the outer surface. The electrode structure may include a LCP substrate defining a first major surface and a second major surface substantially opposite the first major surface, a contact pad disposed on the first major surface, and an electrode disposed on the second major surface. The LCP substrate may be attached to the LCP outer housing and the contact pad may be electrically coupled to the electrical feedthrough.

20 Claims, 7 Drawing Sheets

(56) References Cited

U.S. PATENT DOCUMENTS

| | | | |
|---|---|---|---|
| 2004/0225213 A1 | 11/2004 | Wang et al. | |
| 2006/0009815 A1 | 1/2006 | Boveja et al. | |
| 2008/0033500 A1* | 2/2008 | Strother et al. | 607/36 |
| 2008/0051862 A1 | 2/2008 | Mech et al. | |
| 2009/0275697 A1 | 11/2009 | Waggoner et al. | |
| 2010/0243844 A1 | 9/2010 | Peloza et al. | |
| 2011/0029027 A1 | 2/2011 | Wengreen et al. | |
| 2012/0300421 A1* | 11/2012 | Askarinya et al. | 361/757 |

OTHER PUBLICATIONS

Modem Plastics Worldwide, "Notables: 10 Waves of the future" by Modern Plastics Editorial Staff, Sample molding in progress, Sep. 1, 2005, 2 pp.

www.flipchips.com, Tutorial 31—Jun. 2003, "A survey of wafer level hermetic cavity chip scale packages for RF applications," George A. Riley, PhD, 8 pp.

www.foster-miller.com, Project Examples, Packaging for Implantable Electronics, Foster-Miller, Inc., Feb. 15, 2006, 2 pp.

www.machinedesign.texterity.com, "Vacuum-formed films for fit and function," David Midgley, Welch Fluorocarbon Inc., Dover, N.H., Oct. 7, 2004, 2 pp.

www.devicelink.com. MPMN, May 2004, "Liquid-Crystal Polymer Meets the Challenges of RF Power Packaging; The plastic air-cavity packages are hermetically sealed using a proprietary process," Susan Wallace, 2 pp.

www.flipchips.com, "Wafer-level Hermetic Cavity Packaging," originally published in Advanced Packaging Magazine, May 2004. By George A. Riley, 9 pp.

Boston Healthcare Research Service, David J. Edell, PhD, Feb. 15, 2006, 3 pp.

http://crisp.cit.nih.gov/ Abstract, "High-Density Liquid Crystal Polymer Cochlear Electrodes," Scott S. Corbett, Jul. 1, 2003, 2 pp.

(PCT/US2012/035111) PCT Notification of Transmittal of the International Search Report and the Written Opinion of the International Searching Authority, Mailed Feb. 19, 2013, 21 pages.

* cited by examiner

ELECTRODE STRUCTURE FOR IMPLANTABLE MEDICAL DEVICE

TECHNICAL FIELD

The disclosure relates to implantable medical devices and, more particularly, to configurations of implantable medical devices.

BACKGROUND

An implantable medical device (IMD) may include circuitry disposed within a hermetic, biocompatible outer housing. Some IMD outer housings are formed of biocompatible metals, such as titanium or biocompatible ceramics. Other materials for IMD outer housings have been proposed, such as biocompatible polymers, (e.g., a liquid crystal polymer (LCP)).

SUMMARY

In general, the disclosure is directed to electrical feedthroughs and electrode structures that may be used with an IMD that includes a LCP outer housing. Electrical feedthroughs may extend through the LCP outer housing and provide an electrically conductive pathway for signals to be transferred between circuitry positioned within the LCP outer housing and an exterior of the LCP outer housing. In this way, an electrical feedthrough may connect circuitry within the IMD to an electrode structure positioned on an outer surface of the LCP outer housing or to a conductor within a medical lead.

Described herein are electrical feedthrough geometries and techniques for forming electrical feedthroughs that may be used in IMDs having LCP outer housings. The electrical feedthroughs described herein may facilitate formation of a hermetic seal between the electrical feedthrough and the LCP outer housing and may substantially prevent moisture ingress into the interior (e.g., the space defined by the outer housing) of the IMD.

Also described herein are electrode structures disposed on an exterior of an LCP outer housing of an IMD and techniques for forming electrode structures. The electrode structures and techniques for forming electrode structures described herein may facilitate attachment of electrode structures to the LCP outer housing. In some examples, the electrode structures and techniques for forming electrode structures may also contribute to hermiticity of the LCP outer housing, for example, by providing a hermetic seal between the electrode structure and the LCP outer housing.

In a further aspect, the disclosure is directed to an IMD including a LCP outer housing defining an outer surface of the IMD, an electrical feedthrough extending through the LCP outer housing to the outer surface, and an electrode structure disposed on the outer surface. According to this aspect of the disclosure, the electrode structure comprises a LCP substrate defining a first surface and a second surface substantially opposite the first surface, a contact pad disposed on the first surface, and an electrode disposed on the second surface. The LCP substrate may be attached to the LCP outer housing and the contact pad may be electrically coupled to the electrical feedthrough.

In another aspect, the disclosure is directed to a method including attaching an electrode structure to an outer surface of a liquid crystal polymer (LCP) housing. According to this aspect of the disclosure, the electrode structure comprises an LCP substrate defining a first surface and a second surface substantially opposite the first surface, a contact pad disposed on the first surface, and an electrode disposed on the second surface. The method may further include electrically connecting the contact pad to an electrical feedthrough that extends through the LCP outer housing to the outer surface of the LCP outer housing.

In an additional aspect, the disclosure is directed to an IMD that includes a LCP outer housing defining an outer surface of the IMD, where the outer surface comprises a depression formed in the outer surface. In accordance with this aspect of the disclosure, the IMD also includes a power source encapsulated within the LCP outer housing, and an electrical feedthrough extending through the LCP outer housing to the depression. The electrical feedthrough may form at least a portion of a surface of the depression. Additionally, the IMD may include an electrode structure disposed on the surface of the depression and at least a portion of the outer surface surrounding the depression, and the electrode structure may be electrically connected to the electrical feedthrough at the surface of the depression.

In a further aspect, the disclosure is directed to a method including forming a depression in an outer surface of a LCP outer housing of an IMD to expose an electrical feedthrough. According to this aspect of the disclosure, the LCP outer housing encapsulates a power source, and the electrical feedthrough extends through the LCP outer housing to the depression. The method also may include disposing an electrode structure on a portion of the outer surface and within the depression, and the electrode structure may be electrically connected to the electrical feedthrough exposed within the depression.

In another aspect, the disclosure is directed to an IMD including means for defining an outer surface of the IMD and means for electrically connecting circuitry disposed within the means for defining the outer surface to means for electrically conducting disposed on the outer surface. According to this aspect of the disclosure, the means for electrically connecting extends through the means for defining the outer surface to the outer surface. Additionally, in accordance with this aspect of the disclosure, the means for electrically conducting includes means for defining a first surface and a second surface substantially opposite the first surface. The means for electrically conducting also may include, disposed on the first surface, means for making electrical connection between the means for electrically connecting and the means for electrically conducting. Further, the means for electrically conducting may include, disposed on the second surface, means for conducting electrical signals, and the means for defining the first surface and the second surface may be attached to the means for defining the outer surface.

In an additional aspect, the disclosure is directed to an IMD including means for defining an outer surface of the IMD and a depression in the outer surface of the IMD, means for providing power encapsulated within the means for defining the outer surface, means for electrically connecting the power source to the depression, and means for conducting electrical signals disposed on the surface of the depression and at least a portion of the outer surface surrounding the depression. In accordance with this aspect of the disclosure, the means for electrically connecting extends through the means for defining the outer surface to the depression and forms at least a portion of a surface of the depression. Additionally, the means for conducting electrical signals is electrically connected to the means for electrically connecting the power source to the depression at the surface of the depression.

The details of one or more examples are set forth in the accompanying drawings and the description below. Other features, objects, and advantages of the disclosure will be apparent from the description and drawings, and from the claims.

DETAILED DESCRIPTION

The disclosure is directed to an IMD that includes a LCP outer housing, and configurations of electrical feedthroughs and electrode structures of the IMD. An LCP outer housing for an IMD may provide advantages over other biocompatible materials, such as titanium. For example, LCP may provide a hermetic or near-hermetic enclosure, while also being substantially transparent to RF magnetic field energy, which may facilitate wireless telemetry with or wireless charging of the IMD. LCP may also facilitate forming housing with a relatively wide variety of shapes compared to other IMD housing materials because, for example, LCP may be molded or shaped more readily than some metals or ceramics.

Figure 1:
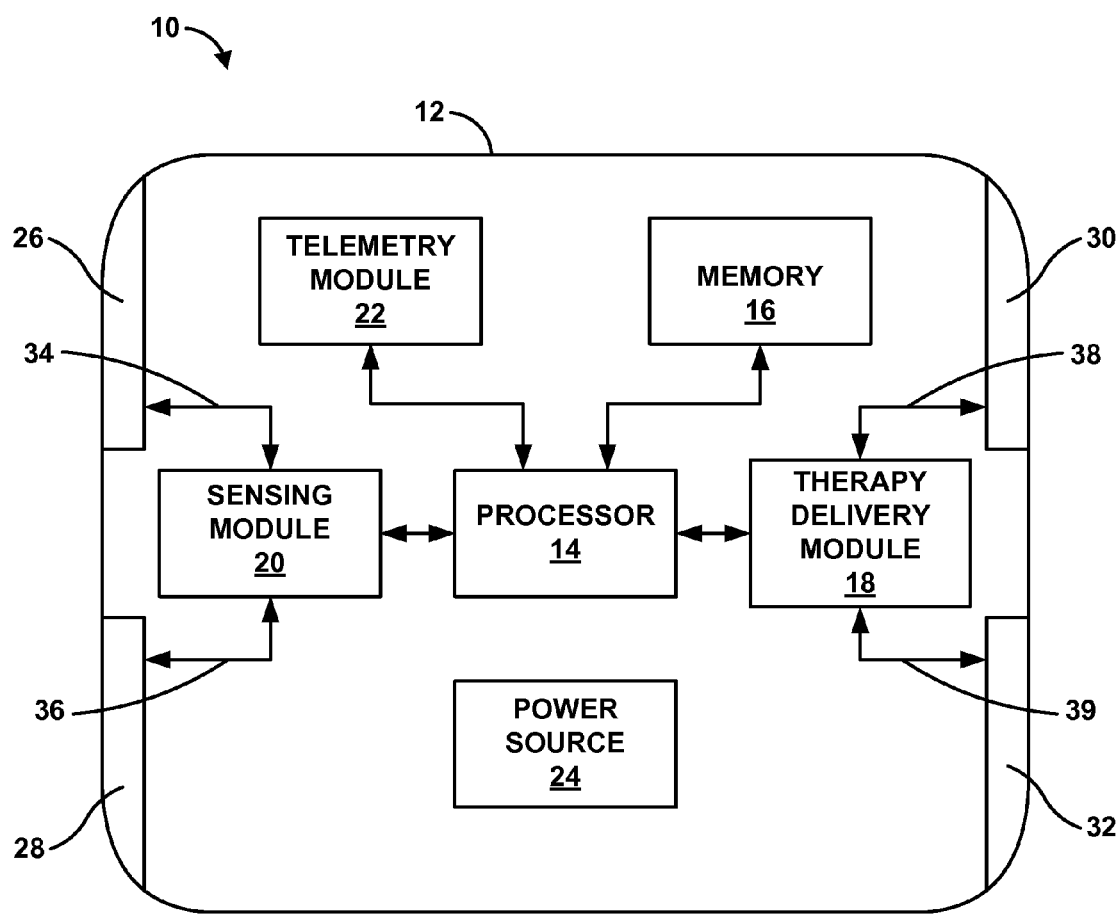
FIG. 1 is a functional block diagram illustrating an example IMD.

FIG. 1 is a functional block diagram that illustrates an example configuration of an IMD 10 in accordance with aspects of the disclosure. In the illustrated example, IMD 10 includes LCP outer housing 12, processor 14, memory 16, therapy delivery module 18, sensing module 20, telemetry module 22, and power source 24. Processor 14, memory 16, therapy delivery module 18, sensing module 20, telemetry module 22, and power source 24 may be disposed within LCP outer housing 12 in some examples, as shown in FIG. 1. In some examples, an outer surface of LCP housing 12 may define an outer surface of IMD 10, e.g., may define a surface that comes into contact with tissue and/or body fluids when implanted in a patient. However, in some cases, a coating or another layer of material may be applied over LCP housing 12. However, even in those examples, housing 12 may define a form factor for IMD 10.

IMD 10 may be any implantable device that is configured to deliver therapy (e.g., electrical stimulation therapy) to a patient or sense a physiological parameter of a patient. In some examples, the patient may be a human patient. In other examples, the patient may be another mammal or other animal. In some examples, IMD 10 may be an implantable cardiac device that generates and delivers cardiac rhythm management therapy to a heart of a patient and senses cardiac electrical activity of the heart. For example, IMD 10 may include an implantable pacemaker, cardioverter, and/or defibrillator that is configured to provide therapy to a heart of the patient via electrodes 30, 32. In some examples, IMD 10 may deliver pacing pulses, but not cardioversion or defibrillation shocks, while in other examples, IMD 10 may deliver cardioversion or defibrillation shocks, but not pacing pulses. In addition, in further examples, IMD 10 may deliver pacing pulses, cardioversion shocks, and defibrillation shocks.

In some examples, IMD 10 may include an implantable neurostimulator (INS), which delivers electrical stimulation to a nerve or other tissue site of a patient and, optionally, senses a physiological parameter of the patient. The INS may deliver, for example, spinal cord stimulation, deep brain stimulation, peripheral nerve stimulation, pelvic floor stimulation, gastric stimulation, or the like.

In other examples, in addition to or instead of a medical device that is configured to deliver therapy to a patient, IMD 10 may be an implantable sensing device, which is configured to sense at least one physiological parameter of a patient. For example, IMD 10 may be configured to sense cardiac electrical activity, neurological electrical activity, physiological conditions such as conditions related to incontinence, urgency, gastroparesis, or the like, via one or more sensors. In some examples, a sensor may be located outside of LCP outer housing 12 of IMD 10 and may be electrically connected to processor 14 of IMD 10, e.g., via an electrical feedthrough that extends through LCP outer housing 12, as described in more detail below.

Memory 16 includes computer-readable instructions that, when executed by processor 14, cause IMD 10 and processor 14 to perform various functions attributed to IMD 10 and processor 14 herein. Memory 16 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 14 may include any one or more processors, including any of a microprocessor, a controller, a digital signal processor (DSP), an application specific integrated circuit (ASIC), a field-programmable gate array (FPGA), or equivalent discrete or analog logic circuitry. In some examples, processor 14 may include multiple components, such as any combination of one or more microprocessors, one or more controllers, one or more DSPs, one or more ASICs, and/or one or more FPGAs, as well as other discrete or integrated logic circuitry. The functions attributed to processor 14 herein may be embodied as software, firmware, hardware or any combination thereof.

In some examples, processor 14 may be capable of (e.g., configured to) determining electrical activity of the patient's heart via sensing module 20 and sensing electrodes 26, 28; providing electrical stimulation (e.g., pacing stimulation, defibrillation stimulation, and/or cardioversion stimulation to the patient's heart) to a patient via therapy delivery module 18 and electrodes 30, 32; communicating wirelessly with a programmer or another device via telemetry module 22; allowing charging of power source 24 (if rechargeable) by an external charging device; or the like. Processor 14 controls therapy delivery module 18 to deliver stimulation therapy to a patient's heart according to a selected one or more of therapy programs, which may be stored in memory 16. For example, processor 14 may control therapy delivery module 18 to deliver electrical pulses with the amplitudes, pulse widths, frequency, or electrode polarities specified by the selected one or more therapy programs.

In the example illustrated in FIG. 1, therapy delivery module 18 is electrically coupled to electrodes 30 and 32, which are disposed on an external surface of LCP outer housing 12. For example, as discussed below with respect to FIGS. 5-10, electrodes 30 and 32 (as well as electrodes 26, 28) may be mechanically coupled to an outer surface of LCP outer housing 12 using any suitable technique. In examples in which electrodes 30 and 32 are disposed on housing 12, therapy delivery module 18 may be electrically connected to electrode 30 via electrical feedthrough 38 and electrode 32 via electrical feedthrough 39. Electrical feedthroughs 38 and 39 extend through LCP outer housing 12 of IMD 10 to an external surface of housing 12 and define an electrically conductive pathway through LCP housing 12. For example, electrical feedthroughs 38, 39 may extend from a first end disposed within a cavity defined by LCP outer housing 12 to a second end proximate to the external surface of LCP outer housing 12. As another example, electrical feedthroughs 38, 39 may extend from a first end disposed proximate to (e.g., adjacent to or mechanically connected to) circuitry of therapy delivery module 18 to a second end proximate to the external surface of LCP outer housing 12. In this example, the first end may be closer to circuitry of therapy delivery module 18 than the second end of the feedthrough.

In some examples, instead of or in addition to being electrically connected to electrodes 30, 32 disposed on the outer surface of LCP outer housing 12, therapy delivery module 18 may be electrically connected to one or more electrodes that are carried by one or more medical leads, e.g., via an electrical feedthrough 38, 39 and at least one conductor carried by the one or more leads. The one or more medical lead may include a proximal end that comprises a connector that electrically connects to an electrical feedthrough 38, 39 proximate to the outer surface of LCP outer housing 12 and a distal end that includes one or more electrodes. The medical lead may include at least one conductor that connects the connector to the one or more electrode. The distal end that includes one or more electrode may be positioned at a target tissue site within the patient, e.g., at a location where electrical stimulation therapy and/or sensing of a physiological parameter is desired.

In the illustrated example, therapy delivery module 18 is configured to generate and deliver electrical stimulation therapy to a patient's heart. For example, therapy delivery module 18 may deliver electrical stimulation to the heart via electrodes 30 and 32. In some examples, therapy delivery module 18 delivers pacing pulses, and cardioversion and/or defibrillation stimulation in the form of electrical shocks. In some examples, therapy delivery module 18 may include separate circuits for delivery of cardiac pacing and cardioversion/defibrillation.

The number and configuration of electrodes 30, 32 shown in FIG. 1 is merely one example. Other configurations of electrodes with which therapy delivery module 18 may deliver electrical stimulation therapy to a patient are contemplated. For example, in some examples, IMD 10 may include more than two electrodes 30 and 32 disposed on the external surface of LCP outer housing 12, may include more than two electrodes carried by at least one medical lead, or may include more than two electrodes in a combination of electrodes disposed on an external surface of housing 12 and electrodes carried by at least one lead. In some examples, each electrode 30 and 32 and/or each conductor of a lead is electrically connected to therapy delivery module 18 via a separate electrical feedthrough (e.g., feedthroughs 38, 39). In some examples, therapy delivery module 18 may include a switch module and processor 14 may use the switch module to select, e.g., via a data/address bus, which of the available electrodes are used to deliver cardioversion or defibrillation therapy or pacing therapy. The switch module may include a switch array, switch matrix, multiplexer, or any other type of switching device suitable to selectively couple stimulation energy to selected electrodes. Additionally or alternatively, IMD 10 may include at least two therapy delivery modules that are coupled to respective electrodes 30, 32 (or respective sets of a plurality of electrodes).

In some examples, sensing module 20 is configured to monitor signals from at least one of sensing electrodes 26 and 28 in order to monitor a physiological parameter of a patient, such as electrical activity of the patient's heart. The number and configuration of sensing electrodes 26, 28 shown in FIG. 1 is merely one example; other configurations are contemplated. For example, in some examples, sensing module 20 may be coupled to more than two sensing electrodes 26 and 28. In the example shown in FIG. 1, sensing electrodes 26 and 28 are disposed on an external surface of LCP outer housing 12. In examples in which sensing electrodes 26 and 28 are disposed on housing 12, sensing module 20 may be electrically connected to sensing electrode 26 via electrical feedthrough 34 and sensing electrode 28 via electrical feedthrough 36.

Electrical feedthroughs 34 and 36 extend through LCP outer housing 12 to an external surface of housing 12 and define an electrically conductive pathway through LCP outer housing 12. For example, electrical feedthroughs 34, 36 may extend from a first end disposed within a cavity defined by LCP outer housing 12 to a second end proximate to the external surface of LCP outer housing 12. In this example, the first end may be closer to the circuitry of sensing module 20 than the second end. As another example, electrical feedthroughs 34, 36 may extend from a first end disposed proximate to circuitry of sensing module 20 to a second end proximate to the external surface of LCP outer housing 12. In other examples, instead of or in addition to being electrically connected to sensing electrodes 26, 28 disposed on the outer surface of LCP outer housing 12, sensing module 20 may be electrically connected to electrodes that are carried by one or more medical leads, e.g., via an electrical feedthrough and at least one conductor carried by the one or more leads. The lead may be similar or substantially the same as the medical lead described above with reference to electrodes 30, 32.

As discussed above, other electrode configurations are contemplated. In some examples, IMD 10 may include more than two sensing electrodes 26 and 28 disposed on the external surface of LCP outer housing 12, may include more than two sensing electrodes carried by at least one lead, or may include more than two sensing electrodes in a combination of sensing electrodes disposed on an external surface of housing 12 and electrodes carried by at least one lead. In some examples, each sensing electrode 26 and 28 and/or each conductor in a lead is connected to sensing module 20 via a separate electrical feedthrough (e.g., feedthroughs 34, 36). In some examples, sensing module 20 may also include a switch module to select which of the available electrodes are used to sense the cardiac electrical activity, depending upon which electrode combination is used in the current sensing configuration. In some examples, processor 14 may select the electrodes that function as sense electrodes, i.e., select the sensing configuration, via the switch module within sensing module 20.

In some examples, sensing module 20 may include one or more detection channels, each of which may be coupled to a selected electrode configuration for detection of cardiac signals via that electrode configuration. Some detection channels may be configured to detect cardiac events, such as P-waves or R-waves, and provide indications of the occurrences of such events to processor 14, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 14 may control the functionality of sensing module 20 by providing signals via a data/address bus.

Telemetry module 22 includes any suitable hardware, firmware, software or any combination thereof for communicating with another device, such as a medical device programmer (not shown). Under the control of processor 14, telemetry module 22 may receive downlink telemetry from and send uplink telemetry to the programmer with the aid of an antenna, which may be internal and/or external. Processor 14 may provide the data to be uplinked to the programmer and the control signals for the telemetry circuit within telemetry module 22, e.g., via an address/data bus. In some examples, telemetry module 22 may provide received data to processor 14 via a multiplexer.

The various components of IMD 10 are coupled to power source 24, which may include a rechargeable or non-rechargeable battery. A non-rechargeable battery may be selected to last for several years, while a rechargeable battery may be inductively charged from an external device, e.g., on a daily or weekly basis.

The techniques and functions attributed to IMD 10, processor 14, therapy delivery module 18, sensing module 20, and telemetry module 22 may be implemented, at least in part, in hardware, software, firmware or any combination thereof. Even where functionality may be implemented in part by software or firmware, such elements will be implemented in a hardware device. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

In some examples, LCP outer housing 12 may be molded around processor 14, memory 16, therapy module 18, sensing module 20, telemetry module 22, and power source 24 (collectively, "the components of IMD 10") using an overmolding process. In some cases, molding or otherwise forming LCP outer housing 12 around the components of IMD 10 may reduce the size of IMD 10, e.g., by reducing a volume of free space (e.g., unoccupied by components of IMD 10) inside LCP outer housing 12 compared to a pre-formed housing (e.g., a biocompatible metal housing) into which the components are placed. Additionally or alternatively, overmolding or otherwise forming LCP outer housing 12 around the components of IMD 10 may facilitate formation of housing 12 with a predetermined shape, and may allow a wider variety of shapes than, for example, a housing formed of titanium or another metal.

For example, LCP outer housing 12 may be molded to include depressions, protrusions, or other three-dimensional features that provide an ergonomic shape to LCP outer housing 12 and IMD 10 based on a location with the patient's body in which IMD 10 will be implanted. The ergonomic shape may be more comfortable to a patient in which IMD 10 is implanted and/or may be easier to implant in the patient (e.g., less invasive and/or easier to manipulate by the clinician). As another example, LCP outer housing 12 may be molded to include depression, protrusions, or other three-dimensional features that facilitate attachment of electrodes 30, 32 and/or sensing electrodes 26, 28 or that function as fixation elements that interact with tissue of the patient to reduce movement of IMD 10 within the patient's body after implantation of IMD 10. In other examples, LCP outer housing 12 may be formed as a container or shell into which the components of IMD 10 are placed.

*In accordance with some aspects of the disclosure, at least one of electrical feedthroughs 34, 36, 38, and 39 may extend through LCP outer housing 12 from a location proximate at least one of the components of IMD 10 (e.g., therapy module 18 and/or sensing module 20) to a location proximate the external surface of LCP outer housing 12. In this way, electrical feedthroughs 34, 36, 38, and 39 may define an electrically conductive pathway from outside housing 12 to components of IMD 10. While electrical feedthroughs 34, 36, 38, and 39 facilitate electrical communication between components in the interior of LCP outer housing 12 and components exterior to LCP outer housing 12, contact surfaces between LCP outer housing 12 and electrical feedthroughs 34, 36, 38, and 39 may present a pathway for moisture to follow to enter the interior of the LCP outer housing 12. This may be disadvantageous in examples in which LCP outer housing 12 is intended to form a hermetic or near-hermetic seal around the components of IMD 10.

In some examples, one or more (e.g., all) electrical feedthroughs 34, 36, 38, and 39 are configured (e.g., with a specific geometry and/or size) in a manner that helps reduce the ingress of moisture into the interior of LCP outer housing 12 via the interface between a respective one or more feedthrough and LCP outer housing 12. Example geometries of electrical feedthroughs 34, 36, 38, and 39 and techniques for forming electrical feedthroughs 34, 36, 38, and 39 that may be used in an IMD 10 that includes LCP outer housing 12 are described with respect to FIGS. 2-4. Electrical feedthroughs 34, 36, 38, and 39 described herein may facilitate formation of a hermetic seal between electrical feedthroughs 34, 36, 38, and 39 and LCP outer housing 12 and may reduce or even substantially prevent moisture ingress into the interior of IMD 10.

In addition, in some examples, electrode structures (e.g., defining sensing electrodes 26, 28 and/or electrodes 30, 32) of IMD 10 are also configured in manner that may help improve the hermeticity of LCP outer housing 12, for example, by providing a hermetic seal between the electrode structure and LCP outer housing 12. Also described herein are examples of such electrode structures disposed on an exterior of LCP outer housing 12 and techniques for forming the electrode structures that are configured in manner that may help improve the hermeticity of LCP outer housing 12. The electrode structures and techniques for forming electrode structures described herein may facilitate attachment of electrode structures to LCP outer housing 12.

Figure 2:
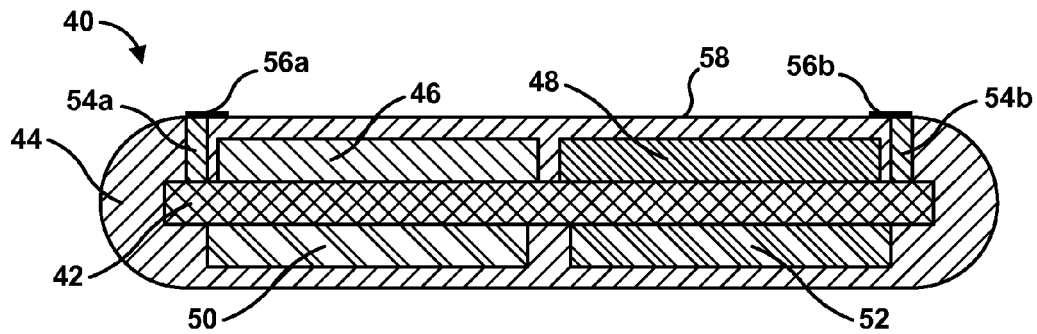
FIG. 2 is a conceptual and schematic cross-sectional diagram illustrating an example IMD.

FIG. 2 is a conceptual cross-sectional diagram illustrating an example IMD 40, which illustrates an example configuration of IMD 10. IMD 40 may include a printed board (PB) 42, an LCP outer housing 44, a power source 46 electrically connected to PB 42, electrical components 48 electrically connected to PB 42, a processor 50 electrically connected to PB 42, and an antenna 52 electrically connected to PB 42. Also shown in FIG. 2 are electrical feedthroughs 54a, 54b (collectively "electrical feedthroughs 54") and electrode structures 56a, 56b (collectively "electrode structures 56"). First electrode structure 56a is disposed on an external surface 58 of LCP outer housing 44 and is electrically connected to first electrical feedthrough 54a. Second electrode structure 56b is disposed on external surface 58 of LCP outer housing 44 and is electrically connected to second electrical feedthrough 54b. Electrode structures 56 may each include an electrically conductive and biocompatible metal or metal alloy. For example, electrode structures 56 may include platinum, silver, gold, titanium, a silver alloy, platinum alloy, gold alloy, a titanium alloy, or the like.

PB 42 may include electrical traces that electrically connect the various devices (also referred to as components) connected to PB 42. In some examples, PB 42 may be a three dimensional PB, and may include electrical traces that run in three dimensions. For example, PB 42 may include a three-dimensional shape configured to accept at least one of power source 46, components 48, processor 50, or antenna 52 within predefined locations or regions of the three-dimensional PB 42. In some examples, PB 42 may be formed at least in part of a LCP, although in other examples, PB 42 may be formed of another material, such as polytetrafluoroethylene, an epoxy, a polyester, or the like.

Power source 46 and processor 50 may be similar to power source 24 and processor 14 described with respect to FIG. 1. Electrical components 48 may include, for example, resistors, capacitors, inductors, or the like, which facilitate operation of IMD 40. For example, electrical components 44 may include high voltage capacitors that are charged from power source 46 in preparation for delivering a defibrillation shock.

Antenna 52 may be electrically connected to processor 50 via PB 42, and may facilitate wireless telemetry with an external device, such as a programmer (not shown). In some examples, antenna 52 may form part of telemetry module 22 shown in FIG. 1. Via antenna 52, processor 50 may receive downlink telemetry from and send uplink telemetry to the programmer Additionally, IMD 40 may include a first electrical feedthrough 54a and a second electrical feedthrough 54b (collectively "electrical feedthroughs 54") electrically connected to PB 42. LCP outer housing 44 encapsulates (e.g., substantially completely surrounds) PB 42, power source 46, components 48, processor 50, antenna 52, and at least a portion of each of electrical feedthroughs 54. For example, LCP outer housing 44 may be overmolded around PB 42, power source 46, components 48, processor 50, antenna 52, and at least a portion of each of electrical feedthroughs 54 to enclose PB 42, power source 46, components 48, processor 50, antenna 52, and at least a portion of each of electrical feedthroughs 54 within LCP outer housing 44. In this way outer surface 58 of LCP outer housing 44 may define and form an outer surface of IMD 40. Electrical feedthroughs 54 are electrically connected to respective electrical traces of PB 42 and electrically connect electrode structures 56 to circuitry of IMD 40 (e.g., processor 50 and/or electrical components 48) via the electrical traces of PB 42.

Electrical feedthroughs 54 may include (e.g., may be formed of and/or defined by) an electrically conductive material, such as a metal or alloy. In some examples, electrical feedthroughs 54 may be formed from a biocompatible, electrically conductive material. For example, electrical feedthroughs 54 may include titanium, platinum, silver, gold, alloys of titanium, platinum, silver, gold, or the like.

In accordance with some aspects of the disclosure, electrical feedthroughs 54 may include a non-uniform width, measured in a substantially similar direction along a plane substantially orthogonal to the length of the electrical feedthrough 54. A length of feedthroughs 54 extends from a first end of the feedthrough (e.g., proximate to PB 42) to a second end of the feedthrough (e.g., proximate to outer surface 58 of LCP outer housing 44). Examples of electrical feedthroughs having non-uniform widths are shown in and described with reference to FIGS. 3A-3J. In contrast to an electrical feedthrough with a non-uniform width, an electrical feedthrough with a uniform width may define only a linear and direct path from outer surface 58 of LCP outer housing 44 to PB 42.

Although not shown in FIG. 2, electrode structures 56 may define a non-planar surface, e.g., may be shaped in three-dimensional space. For example, an outer surface of electrode structures 56, e.g., the surface of electrode structure 56 facing away from outer surface 58 of IMD 40, may include curvature along at least one direction and/or may include at least one projection or depression. In some examples, the non-planar surfaces of electrode structures 56 may define surfaces that contact tissue of a patient when IMD 40 is implanted in the patient. The non-planar surfaces of electrode structures 56 may promote and/or improve tissue-electrode contact when IMD 40 is implanted in a body of a patient compared to a planar electrode surface.

In accordance with some aspects of the disclosure, the configuration of electrode structures 56 may facilitate attachment of the electrode structures 56 to LCP outer housing 44. In some examples, electrode structures 56 may include an LCP substrate, an electrode disposed on a first surface of the LCP substrate, and an electrically conductive contact pad disposed on a second surface of the LCP substrate. In some examples, the LCP substrate may be attached to LCP outer housing 44 to form a hermetic seal between LCP substrate and LCP outer housing 44, and the electrically conductive contact pad may be electrically connected to one of electrical feedthroughs 54. In other examples, electrode structures 56 may include a layer of metal or metal alloy disposed over a depression (not shown in FIG. 2) formed in outer surface 58 of housing 44. Optionally, in some implementations electrode structures 56 may further include an electrically conductive fill material and a second layer of metal or metal alloy disposed over the electrically conductive fill. In some examples, electrode structures 56 may contribute to hermiticity of LCP outer housing 44, for example, by providing a hermetic seal between electrode structures 56 and LCP outer housing 44. Examples of electrode structures 56 and techniques for forming electrode structures are shown in and described with reference to FIGS. 5-10.

FIGS. 3A-3J are conceptual diagrams illustrating example geometries of electrical feedthroughs 60, which may be used as electrical feedthroughs (34, 36, 38, 39, 54) in IMD 10 or IMD 40. Electrical feedthroughs 60 may define a pathway through which an electrical connection can be made between circuitry disposed within LCP outer housing 12, 44, such as therapy delivery module 18 or sensing module 20 of IMD 10, or components 48 or processor 50 of IMD 40, and an electrically conductive element located exterior to LCP outer housing 12, such as sensing electrodes 26, 28 or electrodes 30, 32 of IMD 10, or electrodes 56 of IMD 40. For example, a first end of each of the electrical feedthroughs 60 may be disposed at a location proximate to the circuitry (e.g., connected to the circuitry) and a second end of the electrical feedthrough may be disposed proximate to an outer surface of LCP outer housing 12, 44. In each example, electrical feedthroughs 60 each includes a non-uniform width, where the width of each electrical feedthrough is measured in a substantially similar direction along a plane substantially orthogonal to the length of the respective one of electrical feedthroughs 60.

Figure 3A:
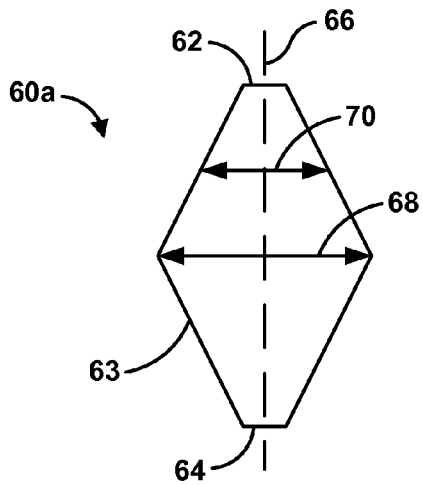
FIGS. 3A-3J are conceptual diagrams illustrating example electrical feedthroughs that include a non-uniform width.

FIG. 3A illustrates an electrical feedthrough 60a that includes a first end 62 and a second end 64. Electrical feedthrough 60a defines a major axis 66 that extends between first end 62 and second end 64. Electrical feedthrough 60a also includes sidewall 63, which defines an outer surface of electrical feedthrough 60a and extends between first end 62 and second end 63. In the example of FIG. 3A, sidewall 63 is not parallel to major axis 66, and, as a result, electrical feedthrough 60a has a non-uniform width, which is measured in a direction along a plane substantially orthogonal to major axis 66. For example, a first width 68 of electrical feedthrough 60a, which is measured in a direction along a first plane substantially orthogonal to major axis 66 is different than a second width 70 of electrical feedthrough 60a, measured in substantially the same direction along a second plane substantially orthogonal to major axis 66. The first plane and the second plane may be substantially parallel, and each plane is substantially orthogonal to major axis 66, but at different points of major axis 66.

FIG. 3A illustrates an example of a shape (generally hexagonal) that electrical feedthrough 60a may have in the plane shown in FIG. 3A. However, electrical feedthrough 60a may any suitable shape in the plane shown in FIG. 3A.

FIG. 3A is a side view of electrical feedthrough 60a, and does not illustrate the shape of electrical feedthrough 60a in the first plane or the second plane substantially orthogonal to major axis 66. In some examples, the shape of electrical feedthrough 60a in the first plane may be the same as the shape of electrical feedthrough 60a in the second plane. In other examples, the shape of electrical feedthrough 60a in the first plane may be different than the shape of electrical feedthrough 60a in the second plane. In general, electrical feedthrough 60a may have any suitable shape in the first plane and the second plane. For example, electrical feedthrough 60a may have a circular cross-section, an elliptical cross-section, a square cross-section, a rectangular cross-section, a triangular cross-section, or any other suitable cross-sectional shape. In examples in which electrical feedthrough 60a includes a circular cross-section, the width of electrical feedthrough 60a in a direction along a plane substantially orthogonal to major axis 66 may be a diameter of electrical feedthrough 60a at the point at which plane sections feedthrough 60a.

Figure 3B:
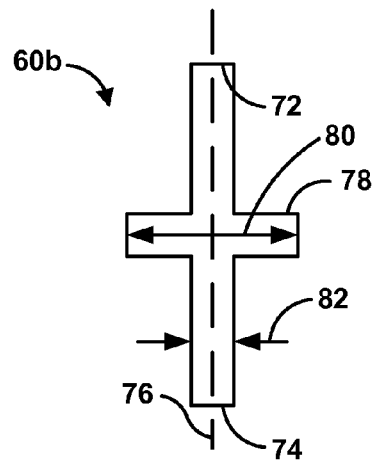

FIG. 3B is a conceptual diagram illustrating another example geometry of an electrical feedthrough 60b. Electrical feedthrough 60b includes a first end 72 and a second end 74, and defines a major axis 76 extending from first end 72 to second end 74. Electrical feedthrough 60b also includes a radial projection 78 extending radially away from major axis 76. In some examples, radial projection 78 forms a single, continuous radial projection that extends around the circumference or perimeter of electrical feedthrough 60b. In other examples, radial projection 78 includes at least two discrete projections that do not form a continuous radial projection around the circumference or perimeter of electrical feedthrough 60b. In some examples, a longitudinal axis of projection 78 may be substantially perpendicular to major axis 76.

Similar to electrical feedthrough 60a of FIG. 3A, electrical feedthrough 60b of FIG. 3B includes a non-uniform width, measured in a direction along a plane substantially orthogonal to major axis 76. For example, electrical feedthrough 60b includes a first width 80 measured in a direction along a first plane substantially orthogonal to major axis 76 at a point where radial projection 78 extend radially away from major axis 76. Width 80 is the width of radial projection 78 in the example shown in FIG. 3B. Electrical feedthrough 60b also include a second width 82, measured in a direction along a second plane that is substantially orthogonal to major axis 76 at a point different from where radial projection 78 extend radially away from major axis 76. First width 80 is different than second width 82.

Similar to electrical feedthrough 60a, electrical feedthrough 60b may include any suitable cross-sectional shape in the first plane or the second plane substantially orthogonal to major axis 76, and the cross-sectional shape of electrical feedthrough 60b may be the same or may be different in the first plane and the second plane.

Figure 3C:
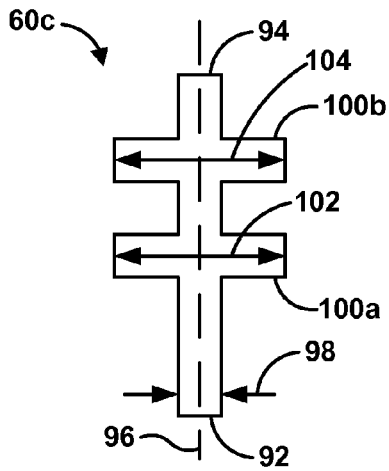

FIG. 3C is a conceptual diagram illustrating another example geometry of an electrical feedthrough 60c, which is similar to electrical feedthrough 60b, but includes two radial projections. Similar to electrical feedthrough 60b, electrical feedthrough 60c may include a first end 92 and a second end 94. Electrical feedthrough 60c may define a major axis 96 extending between first end 92 and second end 94. Electrical feedthrough 60c also includes a first radial projection 100a and a second radial projection 100b (collectively "radial projections 100"). As illustrated in FIG. 3C, first radial projection 100a is a continuous radial projection that extends around the perimeter or circumference of electrical feedthrough 60c (e.g., the portion of feedthrough 60c extending between first and second ends 92, 94, respectively). However, in some examples, as described above with respect to radial projections 78 of FIG. 3B, first radial projection 100a may include at least two discrete radial projections (e.g., projections that extend in substantially opposite directions relative to major axis 96). Similarly, second radial projection 100b is illustrated as a continuous radial projection that extends around the perimeter or circumference of electrical feedthrough 60c, but in other examples, may include at least two discrete radial projections. In some examples, first radial projection 100a and second radial projection 100b include the same number of continuous or discrete radial projections. In other examples, first radial projection 100a includes a different number of continuous or discrete radial projections than second radial projection 100b.

Electrical feedthrough 60c includes a non-uniform width, measured in a direction along a plane substantially orthogonal to major axis 96. For example, electrical feedthrough 60c defines a first width 98 measured in a direction along a first plane substantially orthogonal to major axis 96. First width 98 may be measured at a first point on major axis 96 where a radial projection 100a, 100b does not extend radially away from major axis 96. Electrical feedthrough 60c also defines a second width 102 measured in the same direction along a second plane substantially orthogonal to major axis 96. Second width 102 may be measured at a second point on major axis 96 where first radial projection 100a extends radially away from major axis 96. Electrical feedthrough 60c further defines a third width 104 measured in the same direction along a third plane substantially orthogonal to major axis 96. Third width 104 may be measured at a third point on major axis where second radial projection 100b extends radially away from major axis 96. Although second width 102 and third width 104 are depicted as being approximately equal, in other examples, second width 102 and third width 104 may be different, and each of second width 102 and third width 104 may be different that first width 98.

Similar to electrical feedthrough 60a, the cross-sectional shape of electrical feedthrough 60c (in a plane substantially orthogonal to major axis 96) may be similar along the length of major axis 96, or may be different at different points along major axis 96. For example, the cross-sectional shape of electrical feedthrough 60c may be the same or may be different in the first plane, the second plane, and/or the third plane.

Figure 3D:
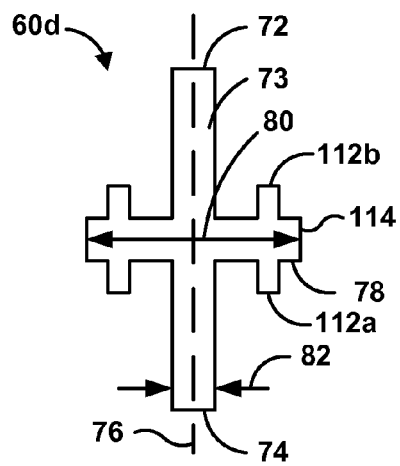

FIG. 3D is a conceptual diagram illustrating another example geometry of an electrical feedthrough 60d. Electrical feedthrough 60d is generally similar to electrical feedthrough 60b of FIG. 3B. However, electrical feedthrough 60d further includes a first axial projection 112a and a second axial projection 112b (collectively "axial projections 112") extending axially from radial projection 78. As illustrated in FIG. 3D, radial projection 78 is a continuous radial projection that extends around the perimeter or circumference of electrical feedthrough 60d. However, in other examples, as described above with respect to radial projections 78 of FIG. 3B, radial projection 78 may include at least two discrete radial projections.

First axial projection 112a extends axially from radial projection 78 in a first direction and second axial projection 112b extends axially from radial projection 78 in a second direction that is different than the first direction. In some examples, the first and second directions are substantially opposite each other. Further, axial projections 112 extend from radial projection 78 at a point radially inward from an end 114 of radial projection 78. In other examples, at least one of axial projections 112 may extend axially from radial projection 78 at end 114 of radial projection 78 (e.g., as shown in FIG. 3E).

Axial projections 112 may facilitate formation of a hermetic seal between electrical feedthrough 60d and an LCP outer housing of an IMD, e.g., LCP outer housing 44 of FIG. 2. Although FIG. 3D illustrates a single first axial projection 112a extending axially in the first direction, in some examples, electrical feedthrough 60d may include at least two axial projections extending axially from radial projection 78 in the first direction. Similarly, in some examples, electrical feedthrough 60d may include at least two axial projections extending axially from radial projection 78 in the second direction. In some examples, electrical feedthrough 60d may include the same number of axial projections extending axially from radial projection 78 in the first direction and the second direction, while in other examples, electrical feedthrough 60d may include a different number of axial projections extending in the first direction and the second direction.

Additionally or alternatively, while axial projections 112 are illustrated in FIG. 3D as being substantially continuous around major axis 76 (e.g., extending around the entire outer perimeter of main section 73 of feedthrough 60d from which projections 78 extends), in some examples, at least one of first axial projection 112a or second axial projection 112b may be discontinuous around major axis 76 and may include a plurality of discrete axial projections extending in one or both of the first direction or the second direction. In some examples, first axial projection 112a may be continuous and second axial projection 112b may be discontinuous, or second axial projection 112b may be continuous and first axial projection 112a may be discontinuous. In other examples, axial projections 112 may both be continuous or may both be discontinuous.

Figure 3E:
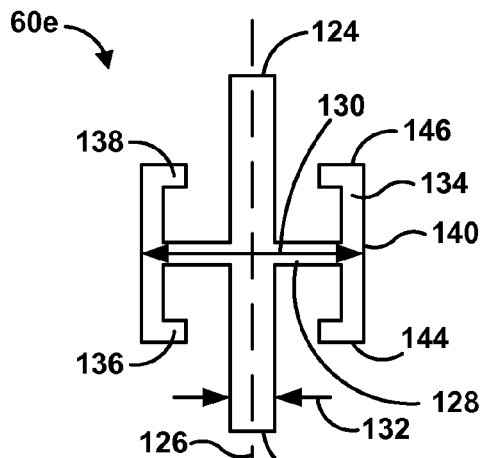

FIG. 3E is a conceptual diagram illustrating another example geometry of an electrical feedthrough 60e. Electrical feedthrough 60e includes a first end 122 and a second end 124, and defines a major axis 126 extending between first end 122 and second end 124. Electrical feedthrough 60d defines a first width 130 measured in a direction along a first plane substantially orthogonal to major axis 126. First width 130 is measured at a first point of major axis 126 where radial projection 128 extends radially away from major axis 132. Electrical feedthrough 60d also defines a second width 132 measured in a direction along a second plane substantially orthogonal to major axis 126. Second width 132 is measured at a second point along major axis 126 where radial projection 128 does not extend radially away from major axis 126. Similar to other electrical feedthroughs described herein, electrical feedthrough 60e may include a non-uniform cross-sectional shape, e.g., the shape of electrical feedthrough 60e in a first plane orthogonal to major axis 126 may be different than the shape of electrical feedthrough 60e in a second plane orthogonal to major axis 126.

Radial projection 128 is illustrated as being continuous around the perimeter or circumference of electrical feedthrough 60e. In other examples, as described above, radial projection 128 may not be continuous, and may include at least two discrete radial projections.

Electrical feedthrough 60e includes an axial projection 134 that extends axially from radial projection 128 at an end 140 of radial projection 128. In the example shown in FIG. 3E, axial projection 134 extends in two different directions away from radial projection 128, such that axial projection 134 is positioned on opposite sides of radial projection 128. Similar to radial projection 128, axial projection 134 is illustrated in FIG. 3E as being continuous around the perimeter or circumference of radial projection, but in other examples, may not be continuous but may include at least two discrete axial projections positioned at different points along radial projection 128. In some examples, electrical feedthrough 60e includes the same number of radial projections and axial projections (i.e., one axial projection for each radial projection), while in other examples, electrical feedthrough 60e may include different numbers of axial projections and radial projections (e.g., more radial projections that axial projections or more axial projections than radial projections).

Electrical feedthrough 60e further includes a first radial projection 136 that extends radially inward (e.g., towards major axis 126 of feedthrough 60e) from a first end 144 of axial projection 134 and a second radial projection 138 that extends radially inward from a second end 146 of axial projection 134. Although FIG. 3E illustrates first radial projection 136 and second radial projection 138 as extending from first end 144 and second end 146, respectively, in other examples, at least one of first radial projection 136 or second radial projection 138 may extend radially inward from axial projection 134 at a point axially closer to radial projection 128 than first end 144 or second end 146, such as a point midway between radial projection 128 and first end 144 or second end 146 of axial projection 134.

Figure 3F:
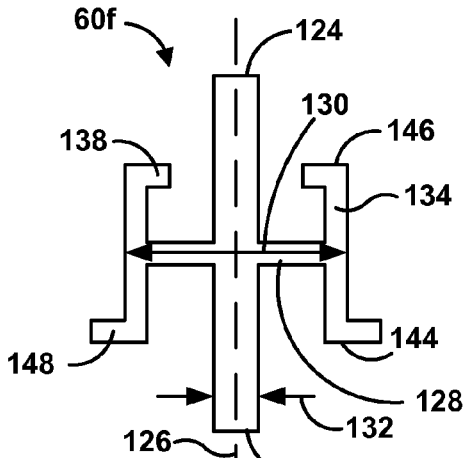

In some examples, at least one of first radial projection 136 or second radial projection 138 may extend radially outward from axial projection 134. For example, FIG. 3F illustrates an electrical feedthrough 60f that includes a first radial projection 148 that extends radially outward from axial projection 134 and a second radial projection 138 that extends radially inward from axial projection 134. Although FIG. 3F illustrates first radial projection 148 as extending from first end 144, in other examples, first radial projection 148 may extend radially outward from axial projection 134 at a point axially closer to radial projection 128 than first end 144 or from second end 146. Other than first radial projection 148, electrical feedthrough 60f of FIG. 3F may be the same or similar to electrical feedthrough 60e of FIG. 3E.

Figure 3G:
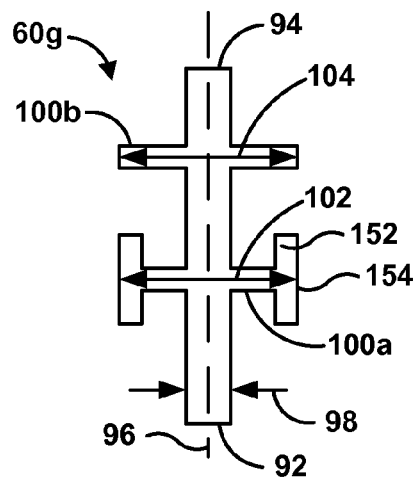

FIG. 3G is a conceptual diagram illustrating another example geometry of an electrical feedthrough 60g. Electrical feedthrough 60g is similar electrical feedthrough 60c of FIG. 3C. However, different from electrical feedthrough 60c, electrical feedthrough 60g includes axial projection 152 extending from an end 154 of first radial projection 100a. As described above with respect to axial projection 134, in other examples, axial projection 152 may extend axially from first radial projection 100a at a point along first radial projection 100a that is radially inward from end 154 (e.g., midway along radial projection 100a between major axis 96 and end 154 of radial projection 100a). Additionally or alternatively, while axial projection 152 is illustrated in FIG. 3G as being substantially continuous around a perimeter or circumference of first radial projection 100a, in other examples, axial projection 152 may be discontinuous and may include at least two axial projections.

In some examples, electrical feedthrough 60g may include at least one axial projection extending from second radial projection 100b instead of or in addition to axial projection 152 extending from first radial projection 100a. Additionally or alternatively, while second width 102 and third width 104 are illustrated as substantially the same, in other examples, second width 102 and third width 104 may be different.

Figure 3H:
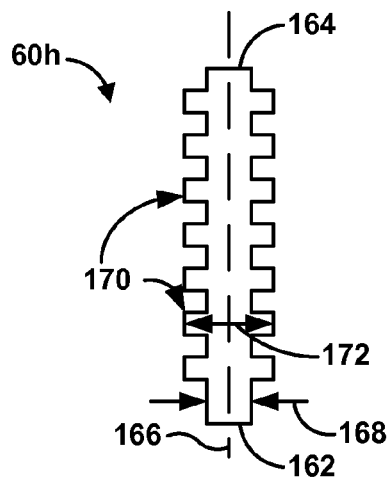

FIG. 3H is a conceptual diagram illustrating another example geometry of an electrical feedthrough 60h. Electrical feedthrough 60h includes a first end 162 and a second end 164. Electrical feedthrough 60h defines a major axis 166 between first end 162 and second end 164. Additionally, electrical feedthrough 60h includes a plurality of radial projections 170. Electrical feedthrough 60h defines a non-uniform width measured in a direction along a plane substantially orthogonal to major axis 166. For example, electrical feedthrough 60h defines a first width 168 measured in the same direction along a second plane that is substantially orthogonal to major axis 166. Electrical feedthrough 60h defines a second width 172 measured in the same direction along a second plane that is substantially orthogonal to major axis 166. The first width 168 is measured at a first point along major axis 166 at a position where a radial projection, e.g., radial projection 170, does not extend radially away from major axis 166. The second width 172 is measured at a second point along major axis 166 at a position where radial projection 170 extends radially away from major axis 166.

Although the width of electrical feedthrough 60h is illustrated as being substantially the same at each of the radial projections 170, this may not be the case in every example. In some examples, the width of electrical feedthrough 60h may be different at one radial projection 170 than a width of electrical feedthrough 60h at another radial projection 170. Similarly, although the width of electrical feedthrough 60h is illustrated as being substantially the same at each point where a radial projection 170 does not extend radially away from major axis 166, in other examples, the width of electrical feedthrough 60h may be different at one position that does not include a radial projection 170 than a width of electrical feedthrough 60h at another position that does not include a radial projection 170.

As described above with respect to FIG. 3A, in some examples, the shape of electrical feedthrough 60h (as well as other electrical feedthroughs described herein) in a plane substantially orthogonal to major axis 166 may be non-uniform along major axis 166. For example, the shape of electrical feedthrough 60h in the first plane may be the same as the shape of electrical feedthrough 60h in the second plane. In other examples, the shape of electrical feedthrough 60h in the first plane may be different than the shape of electrical feedthrough 60h in the second plane. In general, electrical feedthrough 60h may have any shape in the first plane and the second plane.

Figure 3I:
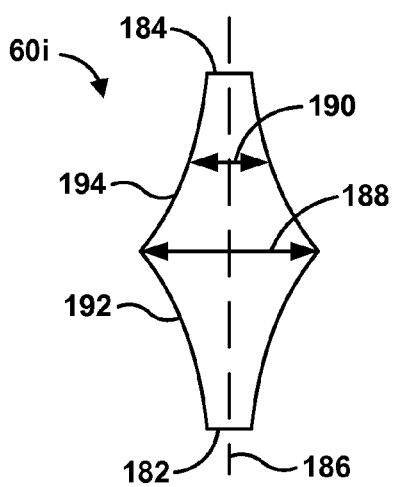

FIG. 3I is a conceptual diagram illustrating another example geometry of an electrical feedthrough 60i. Electrical feedthrough 60i is generally similar to electrical feedthrough 60a of FIG. 3A; however, electrical feedthrough 60i includes a first sidewall 192 that is curved along the direction of major axis 186 and a second sidewall 194 that is also curved along the direction of major axis 186. First sidewall 192 and second sidewall 194 include generally concave curvature in the illustrated example. Other curvatures are contemplated. For example, in other examples, first sidewall 192 and second sidewall 194 may include generally convex curvature, or one of first sidewall 192 and second sidewall 194 may include concave curvature and the other of first sidewall 192 and second sidewall 194 may include convex curvature. Additionally or alternatively, electrical feedthrough 60i may include more than two sidewalls, and hence may include more than two different sections of curvature.

Similar to electrical feedthrough 60a, electrical feedthrough 60i includes a first end 182 and a second end 184. Electrical feedthrough 60i also includes a non-uniform width measured in a direction along a plane substantially orthogonal to major axis 186. For example, electrical feedthrough 60i includes a first width 188 measured in a direction along a first plane substantially orthogonal to major axis 186 and a second width 190 measured in the same direction along a second plane substantially orthogonal to major axis 186. First width 188 and second width 190 are measured at different points along major axis 186 and are different from each other.

As described above, in some examples, electrical feedthrough 60i may include a non-uniform cross-sectional shape in a plane substantially orthogonal to major axis 186.

Figure 3J:
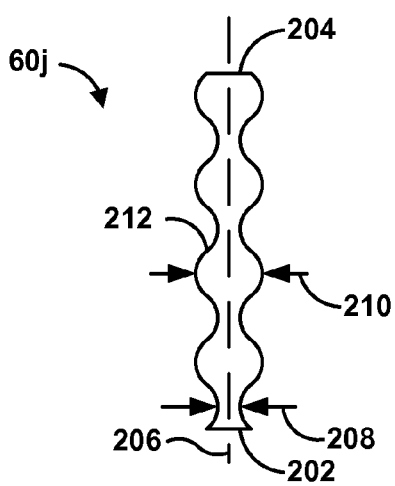

FIG. 3J is a conceptual diagram illustrating another example geometry of an electrical feedthrough 60j. Electrical feedthrough 60j is generally similar to electrical feedthrough 60h of FIG. 3H; however, electrical feedthrough 60j includes a sidewall 212 that is curved along the direction of major axis 206 instead of projections 170 that are generally rectangular. Electrical feedthrough 60j includes a first end 202 and a second end 204 and defines a major axis 206 between first end 202 and second end 204. Electrical feedthrough 60j defines a first width 208 measured in a direction along a first plane substantially orthogonal to major axis 206 and a second width 210 measured in the same direction along a second plane substantially orthogonal to major axis 206. First width 208 is different than second width 210.

Figure 4:
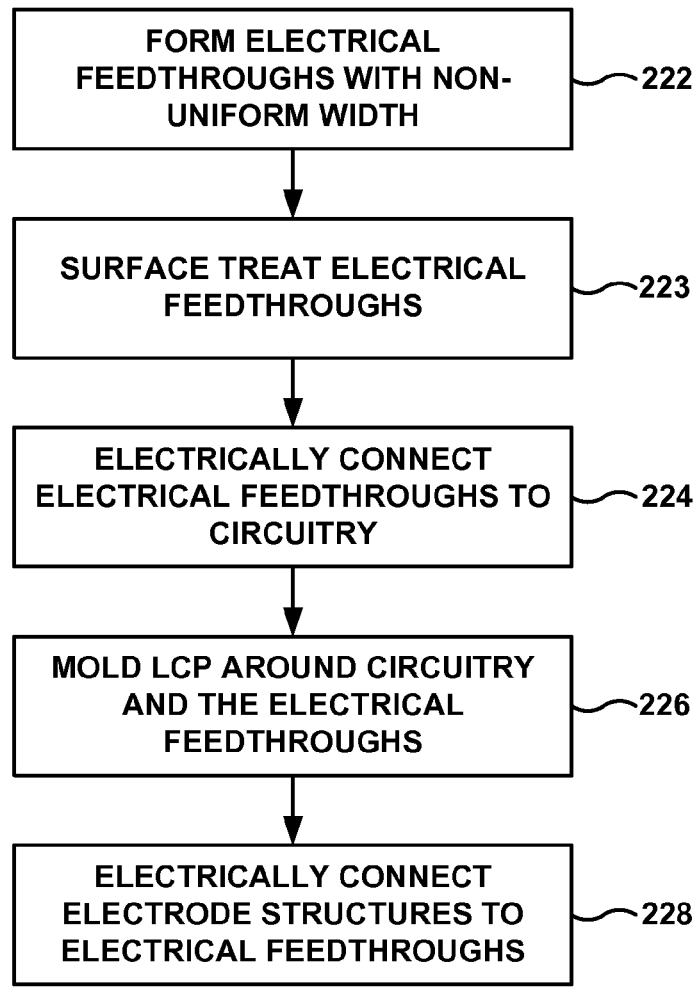
FIG. 4 is a flow diagram that illustrates an example technique that may used to form an IMD that includes an electrical feedthrough that includes a non-uniform width.

FIG. 4 is a flow diagram that illustrates an example technique that may used to form an implantable medical device that includes an electrical feedthrough with a non-uniform width, such as one of electrical feedthroughs 60. The technique of FIG. 4 will be primarily described with reference to IMD 40 of FIG. 2, although reference will also be made to electrical feedthroughs 60 of FIGS. 3A-3J and IMD 10 of FIG. 1. In accordance with the technique of FIG. 4, electrical feedthroughs 54 are formed (222). For example, electrical feedthroughs 54 may be formed (222) by molding, machining, pressing, laser drilling, or the like. Although FIG. 2 illustrates two electrical feedthroughs 54a, 54b, in other examples, IMD 40 may include one electrical feedthrough, e.g., first electrical feedthrough 54a, or may include at least three electrical feedthroughs 54, such as three or more electrical feedthroughs. As described above, electrical feedthroughs 54 may include a non-uniform width, measured in a direction along a plane substantially orthogonal to a major axis of the electrical feedthrough 54 (e.g., see major axis 76, first width 80, and second width 82 of FIG. 3B).

In some examples, an electrical feedthrough 60b (FIG. 3B) comprising a non-uniform width may include at least one radial projection 78, where radial projection 78 defines a first width 80 and electrical feedthrough 60b defines a second width 82 different than first width 80 at a different point along major axis 76. In other examples, an electrical feedthrough 60a may include at least one sloped sidewall 63 (FIG. 3A) or at least one curved sidewall (e.g., sidewalls 192, 194 of electrical feedthrough 60i of FIG. 3I). As described above, electrical feedthroughs 54 may be formed of an electrically conductive material, such as an electrically conductive metal or alloy, which in some examples may be biocompatible.

In some examples, the technique may optionally include surface treating electrical feedthroughs 54 (223). For example, a surface of electrical feedthroughs 54 (e.g., sidewall 63 shown in FIG. 3A) may receive a surface treatment that may promote or improve adherence and formation of a hermetic bond between electrical feedthroughs 54 and LCP outer housing 44. Although FIG. 4 illustrates this step occurring before electrically connecting electrical feedthroughs 54 to circuitry (224), in other examples, surface treating electrical feedthroughs 54 may occur after electrically connecting electrical feedthroughs 54 to circuitry (224).

In some examples, surface treating electrical feedthroughs 54 (225) may include roughening a surface of electrical feedthroughs using a chemical wet etch or a dry etch, e.g., using ion bombardment. In some examples, only portions of a surface of electrical feedthroughs 54 may be etched, and other portions of the surface may be masked to prevent etching.

In some examples, surface treating electrical feedthroughs 54 (225) may include oxidizing a surface of electrical feedthroughs 54.

In some examples, surface treating electrical feedthroughs 54 (225) may include coating electrical feedthroughs 54 with an epoxy or adhesive. The epoxy or adhesive may promote adhesion between electrical feedthroughs 54 and LCP outer housing 44. In some examples, the epoxy or adhesive may be exposed to heat or UV radiation to cure the epoxy or adhesive. The exposure to heat and/or UV radiation may occur after molding LCP outer housing 44 around the circuitry and at least a portion of electrical feedthroughs 54 (226). The exposure of the epoxy or adhesive to heat and/or UV radiation may improve bonding between LCP outer housing 44 and the epoxy or adhesive, and, ultimately, between LCP outer housing 44 and electrical feedthroughs 54.

The technique of FIG. 4 further includes electrically connecting electrical feedthroughs 54 to circuitry (224). The circuitry may include, for example, circuitry of an IMD, such as one or more electrical components 48, processor 50, or an electrical trace of PB 42 (FIG. 2). In this example, electrical feedthroughs 54 are electrically connected to one or more electrical traces of PB 42, and the one or more electrical traces of PB 42 may be electrically connected to at least one of one or more electrical components 48 or processor 50 of IMD 40. In some examples, electrical feedthroughs 54 may be electrically connected to the circuitry via soldering, an electrically conductive adhesive (e.g., a conductive epoxy), or the like.

Once electrical feedthroughs 54 are electrically connected to circuitry (224), LCP outer housing 44 may be molded around the circuitry (e.g., around PB 42, power source 46, electrical components 48, processor 50, and antenna 52) and at least a portion of electrical feedthroughs 54 (226). LCP outer housing 44 may be molded around the circuitry using any suitable technique, such as, but not limited to, injection molding. In some examples, LCP outer housing 44 may be molded around the circuitry and electrical feedthroughs 54 and may substantially encapsulate electrical feedthroughs 54. Molding of LCP outer housing 44 may also define the desired form factor of IMD 40. In examples in which the LCP is deposited over an end of electrical feedthroughs 54 that is opposite the end adjacent the circuitry, a portion of LCP outer housing 44 may be removed to expose a portion of each of the electrical feedthroughs 54 to allow connection of electrodes 56 to feedthroughs 54. In other examples, LCP outer housing 44 may be molded around the circuitry and electrical feedthroughs 54 and may encapsulate a portion of electrical feedthroughs 54, while a portion of each of the electrical feedthroughs 54 is left unencapsulated to facilitate connection of electrode structures 56 to feedthroughs 54.

The technique of FIG. 4 further includes electrically connecting electrode structures 56 to electrical feedthroughs 54 (228). In some examples, electrically connecting electrode structures 56 to electrical feedthroughs 54 (228) may include disposing a metal film or a metal sheet on outer surface 58 of LCP outer housing 44 in a manner that results in contact (directly or indirect, e.g., via an electrically conductive interface material) between the metal film or metal sheet and one of electrical feedthroughs 54. In other examples, electrically connecting electrodes 56 to electrical feedthroughs 54 (228) may include forming an electrode structure, e.g., electrode structure 56a that includes an LCP substrate, a contact pad on a first surface of the LCP substrate, and an electrode on a second surface of the LCP substrate, where the electrode is electrically connected to the contact pad. The contact pad may then be electrically connected to one of electrical feedthroughs 54, e.g., via direct physical contact or via an electrically conductive interface material, and the LCP substrate may be attached to LCP outer housing 44. Further details regarding electrode structures 56 and electrically connecting electrode structures 56 to electrical feedthroughs 54 will be described with respect to FIGS. 5-10.

Figure 5:
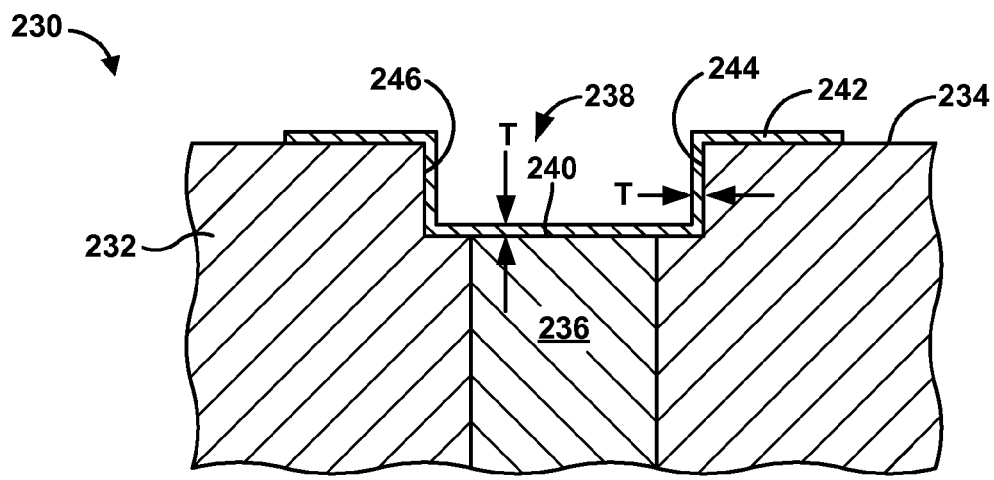
FIG. 5 is a conceptual and schematic cross-sectional diagram illustrating an example IMD including an electrode structure disposed on an outer surface of a LCP outer housing.

As discussed above, in some examples, electrode structures 56 may be configured to provide hermetic or near-hermetic seals between electrode structures 56 and an LCP outer housing of an IMD. FIG. 5 is a conceptual cross-sectional diagram illustrating an example IMD 230 that includes an example of such an electrode structure 242 disposed on a LCP outer housing 232. In some examples, LCP outer housing 232 may be similar to LCP outer housings 12, 44 of IMDs 10, 40, respectively, described above. LCP outer housing 232 includes an outer surface 234 and a depression 238 formed in outer surface 234. In some examples, depression 238 may be formed in outer surface 234 during the manufacturing process of LCP outer housing 232, e.g., during injection molding of LCP outer housing 232. For example, a mold used to define a shape of LCP outer housing 232 may include a feature (e.g., a protrusion) corresponding to the negative of depression 238. In other examples, depression 238 may be formed in outer surface 234 after formation of LCP outer housing 232. For example, depression 238 may be formed using, for example, percussion drilling, rotary drilling, laser ablation, or another technique for controllably removing material from LCP outer housing 232.

In some examples, depression 238 may define a depth (measured from outer surface 234) of up to about 6.35 mm (about 0.25 inch). For example, depression 238 may define a depth of between about 3.175 mm (about 0.125 inch) to about 6.35 mm (about 0.25 inch). As another example, depression 238 may define a depth of between about 4 mm (about 0.1575 inch) to about 5 mm (about 0.1969 inch). In some examples, depression 238 may define a width between about 100 microns (about 0.003937 inch) to about 12.7 mm (about 0.5 inch).

As shown in FIG. 5, depression 238 is formed at a location of outer surface 234 to expose electrical feedthrough 236 at a surface 240 of depression 238. Electrical feedthrough 236 defines an electrically conductive pathway from electrode structure 242 to, e.g., circuitry within LCP outer housing 232. In some, but not all, examples, electrical feedthrough 236 may define a non-uniform width, measured in a direction along a plane substantially orthogonal to a major axis of electrical feedthrough 236, e.g., as described with respect to electrical feedthroughs 60 of FIGS. 3A-3J. In other examples, electrical feedthrough 236 may define a substantially uniform width, such as a substantially uniform diameter. As described above, electrical feedthrough 236 may include an electrically conductive material, such as an electrically conductive metal or alloy, and may in some examples be biocompatible. An end of electrical feedthrough 236 is exposed at surface 240 of depression 238, which allows an electrical connection to be formed between electrical feedthrough 236 and electrode structure 242, and, therefore, from electrode structure 242 to circuitry to which feedthrough 236 is electrically connected.

In some examples, instead of being a separate structure from a PB, electrical feedthrough 236 may be integral to a PB, such as PB 44 of FIG. 2. For example, PB 44 may be formed as a three-dimensional PB (as opposed to a substantially two-dimensional, planar PB), which includes projections that form electrical feedthrough 236.

Electrode structure 242 includes a metal layer disposed on surface 240 of depression 238, walls 244, 246 of depression 238, and a portion of outer surface 234 of LCP outer housing 232. The metal layer may include an electrically conductive metal or alloy, such as, but not limited to, any one or more of platinum, gold, titanium, silver, or an alloy of at least one of these metals and at least one other metal. In some examples, the metal layer may be biocompatible. The metal layer defining electrode structure 242 may be substantially uniform in thickness T. In other examples, the metal layer defining electrode structure 242 may have varying thickness, e.g., may be thicker at the portion that is positioned within depression 238 or at another portion of electrode structure 242.

Figure 7:
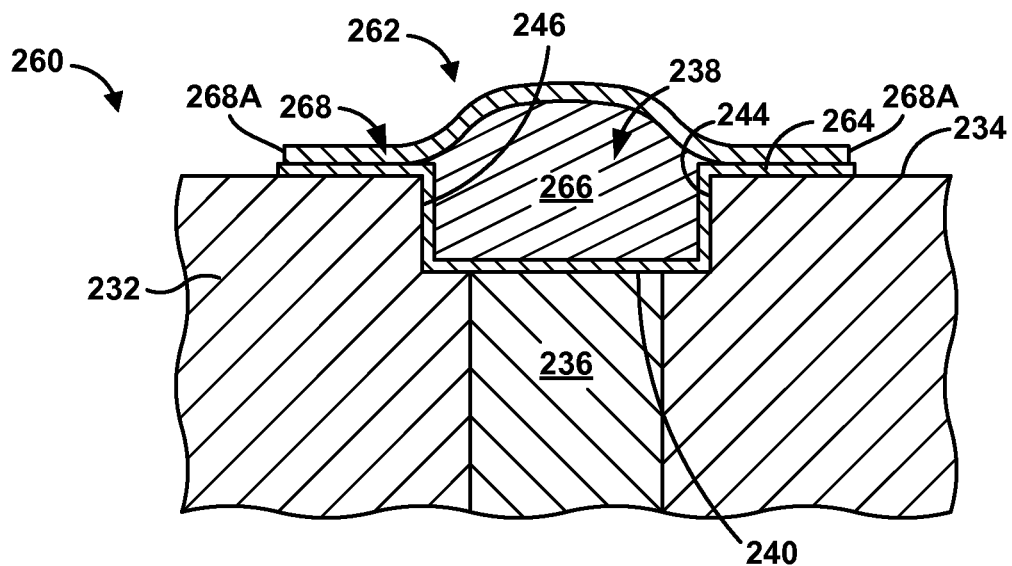
FIG. 7 is a conceptual and schematic cross-sectional diagram illustrating another example IMD including an electrode structure disposed on an outer surface of a LCP outer housing.

In the example shown in FIG. 7, electrode structure 242 is positioned within depression 238 such that it substantially follows the contour of depression 238. Thus, in some examples, electrode structure 242 may substantially reproduce the shape of depression 238, as shown in FIG. 7. In this way, IMD 230 may include a depression. In other examples, electrode structure 242 may have a non-uniform thickness T and may not substantially reproduce the shape of depression 238. For example, electrode structure 242 may at least partially fill depression 238, and in some implementations, may substantially fully fill depression 238.

Figure 6:
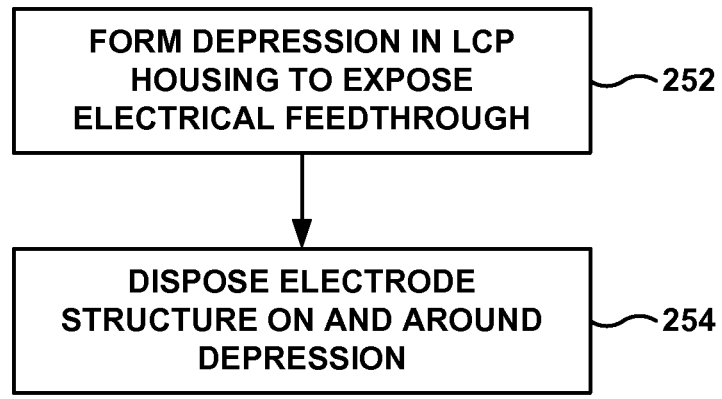
FIG. 6 is a flow diagram that illustrates an example technique that may used to form an IMD that includes the electrode structure shown in FIG. 5.

FIG. 6 is a flow diagram that illustrates an example technique that may be used to form IMD 230 of FIG. 5. The technique includes forming depression 238 in outer surface 234 of LCP outer housing 232, e.g., to expose electrical feedthrough 236 at surface 240 of depression 238 (252). As described above, in some examples, depression 238 may be formed during the molding process used to form LCP outer housing 232, e.g., by using a mold that includes a projection that corresponds to the negative of depression 238. In other examples, depression 238 may be formed by removing material from LCP outer housing 232 after LCP outer housing 232 has been molded. In some examples, electrical feedthrough 236 may be formed within LCP outer housing 232 such that an end of feedthrough 236 that is exposed by depression 238 is set back from the outer surface 234 of LCP outer housing 232, such that removal of some LCP is required to expose feedthrough 236. In other examples, during the formation of depression 238, some material of electrical feedthrough 236 is also removed.

The technique further includes disposing electrode structure 242 on and around depression 238 (254). For example, electrode structure 242 may be disposed on surface 240 of depression 238, walls 244, 246 of depression 238, and a portion of outer surface 234 around depression 238, as shown in FIG. 5. In some examples, electrode structure 242 may be disposed on and around depression 238 using a metal deposition method, such as sputtering, physical vapor deposition (PVD), chemical vapor deposition (CVD), or the like. In other examples, electrode structure 242 may be disposed on and around depression 238 by adhering and/or soldering a preformed metal or alloy film to at least one of surface 240, walls 244, 246, or outer surface 234. For example, electrode structure 242 may be reflow soldered to electrical feedthrough 236 and/or welded or adhered to outer surface 234. In some examples, a seal between electrode structure 242 and outer surface 234 and/or a seal between electrode structure 242 and electrical feedthrough 236 may be hermetic, which may reduce or substantially preventing ingress of moisture or bodily fluids to within LCP outer housing 232, e.g., via the interface between electrical feedthrough 236 and LCP outer housing 232. For example, when electrode structure 242 is formed by sputtering, PVD, or CVD, formation of electrode structure 242 on and around depression 238 may form a hermetic seal between electrode structure 242 and outer surface 234.

In some examples, instead of including a single metal layer, an electrode structure may include multiple layers. For example, an electrode structure may include at least two metal layers, which may have the same or different compositions, disposed over each other. As another example, an electrode structure may include at least one fill material that is disposed over a metal layer to at least partially fill depression 238. FIG. 7 is a conceptual cross-sectional diagram illustrating an example IMD 260 that includes an electrode structure 262 that includes three layers disposed on a LCP outer housing 232. IMD 260 is substantially similar to IMD 230 of FIG. 5, although IMD 260 includes an electrode structure 262 that includes a first metal layer 264, a fill material 266, and a second metal layer 268.

First metal layer 264 may be the same or substantially similar to electrode structure 242 of FIG. 5. For example, first metal layer 264 may include an electrically conductive metal or alloy, such as, but not limited to, any one or more of platinum, gold, titanium, silver, or an alloy of at least one of these metals and at least one other metal. In some examples, first metal layer 264 may be biocompatible. In some examples, first metal layer 264 directly contacts electrical feedthrough 236 at surface 240, and is disposed on surface 240 of depression 238, walls 244, 246 of depression 238, and a portion of outer surface 234. In the example shown in FIG. 7, first metal layer 264 is positioned within depression 238 such that it substantially follows the contour of depression 238. As with electrode structure 242, in some examples, first metal layer 264 may have a substantially uniform thickness, while in other examples, first metal layer 264 may have a non-uniform thickness.

In the example shown in FIG. 7, when first metal layer 264 is positioned within depression 238, first metal layer 264 defines an opening (e.g., a second depression) in which fill material 266 may be positioned. In some examples, electrode structure 262 may include multiple metal layers disposed on and around depression 238 instead of a single first metal layer 264. The multiple metal layers may have the same or different compositions.

Fill material 266 is formed or deposited over at least a portion of first metal layer 264. In some examples, as shown in FIG. 7, fill material 266 may substantially fill depression 238, and may even extend out of depression 238, beyond outer surface 234 of LCP outer housing 232, as shown in FIG. 7. In other examples, fill material 266 may fill only a portion of depression 238 and may not extend out of depression 238 beyond outer surface 234. For example, even after positioning of fill material 266 over first metal layer 264 and within depression 238, a void may still be defined in the outer surface 234 of IMD 260.

In some examples, fill material 266 may include an electrically conductive metal or alloy, such as a tin-gold (Sn—Au), solder or eutectic material that may be reflowed into depression 238 after disposing first metal layer 264 on and around depression 238. In other examples, fill material 266 may include another electrically conductive material, such as an electrically conductive epoxy or other electrically conductive polymer, adhesive, or composite material. In some examples, electrode structure 262 may include multiple layers of fill material 266 instead of a single layer of fill material 266. The multiple layers of fill material 266 may have the same or different compositions. In some examples, fill material 266 may improve adhesion between second metal layer 268 and first metal layer 264 compared to an electrode structure that does not include fill material 266.

Electrode structure 262 further includes a second metal layer 268, which is disposed over fill material 266. Second metal layer 268 may include an electrically conductive and biocompatible metal or metal alloy. In some examples, second metal layer 268 may include the same metal or alloy as first metal layer 264. In other examples, second metal layer 268 may include a different metal or alloy than first metal layer 264. For example, second metal layer 268 may include platinum, gold, titanium, silver, or an alloy of at least one of these metals and at least one other metal. Second metal layer 268 may contact first metal layer 264 around at least a portion of a perimeter of depression 238. For example, as shown in FIG. 7, second metal layer 268 is disposed on first metal layer 264 over a portion of outer surface 234. Second metal layer 268 may have a substantially uniform thickness in some examples, while in other examples, second metal layer 268 may have a non-uniform thickness. For example, second metal layer 268 (and, in some cases, first metal layer 264 as well) may be tapered at its ends 268A, 268B to define a smooth interface between electrode structure 262 and outer surface 234 of LCP housing 232.

In some examples, second metal layer 268 and first metal layer 264 may form a hermetic seal where second metal layer 268 and first metal layer 264 contact each other, e.g., by welding second metal layer 268 to first metal layer 264, or due to the deposition process used to form second metal layer 268 (e.g., sputtering, CVD, or PVD). In some examples, electrode structure may include 262 may include multiple metal layers disposed over fill material 266 instead of a single second metal layer 282. The multiple metal layers may have the same or different compositions. In addition, in some examples, a hermetic seal may be formed between first metal layer 264 and LCP housing 232 of IMD 260.

Figure 8:
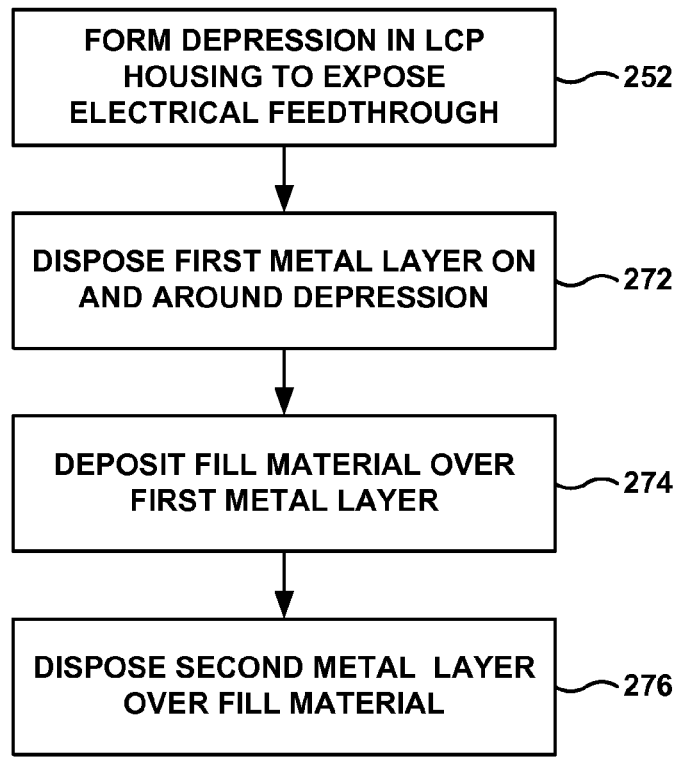
FIG. 8 is a flow diagram that illustrates an example technique that may used to form an IMD that includes the electrode structure shown in FIG. 7.

FIG. 8 is a flow diagram that illustrates an example technique of forming electrode structure 262. As described with respect to FIG. 6, depression 238 may be formed in LCP outer housing 232 to expose a portion of electrical feedthrough 236 (252). Once depression 238 is formed (252), first metal layer 264 may be disposed on and around depression 238 (272). For example, first metal layer 264 may be disposed on surface 240 of depression 238, walls 244, 246 of depression 238, and a portion of first surface 234 around depression 238, as shown in FIG. 7. In some examples, first metal layer 264 may be disposed on and around depression 238 using a metal deposition method, such as PVD, CVD, or the like. In other examples, first metal layer 264 may be disposed on and around depression 238 by adhering and/or soldering a pre-formed metal or alloy film to at least one of surface 240, walls 244, 246, or outer surface 234. For example, first metal layer 264 may be reflow soldered to electrical feedthrough 236 and/or welded or adhered to outer surface 234. In some examples, a seal between first metal layer 264 and outer surface 234 and/or a seal between first metal layer 264 and electrical feedthrough 236 may be hermetic, which may reduce or substantially preventingress of moisture or bodily fluids to within LCP outer housing 232, e.g., via the interface between electrical feedthrough 236 and LCP outer housing 232.

The technique of FIG. 8 may further include depositing fill material 266 over first metal layer 264 (274). As described above, in some implementations, fill material 266 may solder or eutectic material that may be reflowed into depression 238 over first metal layer 264. In other examples, fill material 266 may be deposited using, for example, sputtering, electroless deposition, CVD, PVD, or the like.

Once fill material 266 is deposited over first metal layer 264 (274), second metal layer 268 may be disposed over fill material 266 (276). Second metal layer 268 may be disposed over fill material 266 using a similar process to the process used to form first metal layer 264, e.g., CVD, PVD, or by adhering or welding a metal film comprising second metal layer 268 to first metal layer 264. In some examples, the same process may be used to form second metal layer 268 as was used to form first metal layer 264. In other examples, a first process may be used to form first metal layer 264, and a second, different process may be used to form second metal layer 268.

As described above, in some examples, the process used to form second metal layer 268 over fill material 266 may result in a hermetic seal between first metal layer 264 and second metal layer 268.

Figure 9:
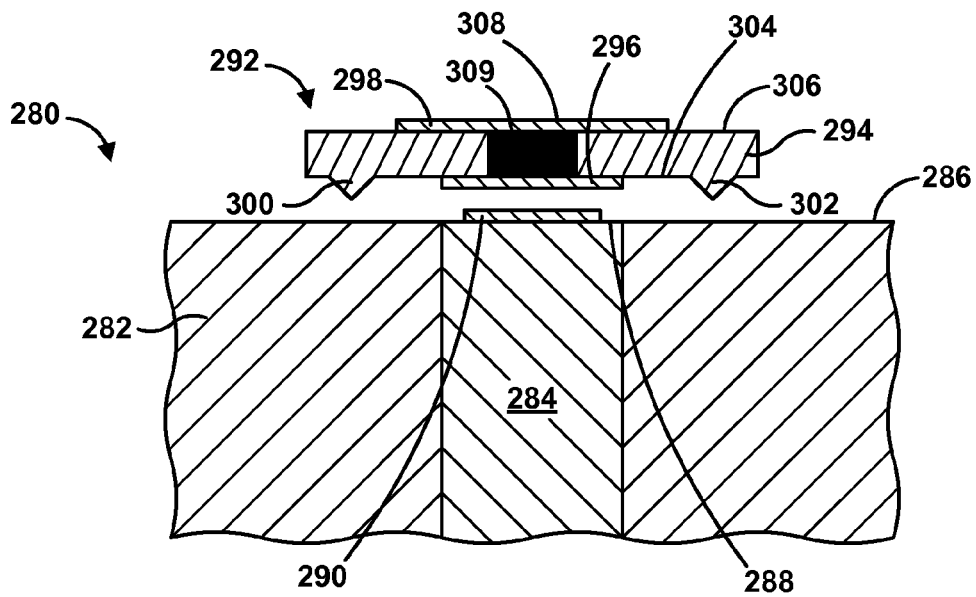
FIG. 9 is a conceptual and schematic cross-sectional diagram illustrating another example IMD including an electrode structure prior to the electrode structure being attached to the IMD.

FIG. 9 illustrates another example electrode structure that may be used with an LCP outer housing of an IMD, where the electrode structure may be configured to facilitate attachment to the LCP outer housing and/or may be configured to contribute to the hermiticity of the LCP outer housing, e.g., by defining a hermetic seal between the structure and the LCP housing. FIG. 9 is a conceptual cross-sectional diagram illustrating an example IMD 280 and an electrode structure 292, prior to electrode structure 292 being attached to IMD 280. IMD 280 includes LCP outer housing 282 and electrical feedthrough 284, which may be the same or similar to LCP outer housing 232 and electrical feedthrough 236 of FIGS. 5 and 7. LCP outer housing 282 defines an outer surface 286 of IMD 280, and electrical feedthrough 284 extends to a first end 288 proximate to first surface 286. In some examples, a second end (not shown) of electrical feedthrough 284 may be proximate circuitry within IMD 280, as described above with respect to FIGS. 2-4.

FIG. 9 also illustrates electrode structure 292, which may include a LCP substrate 294, a contact pad 296 disposed on a first surface 304 of LCP substrate 294, and an electrode 298 disposed on a second surface 306 of LCP substrate 294. LCP substrate 294 includes a first protrusion 300 and a second protrusion 302, which may facilitate attachment of LCP substrate 294 to LCP outer housing 282.

Contact pad 296 is disposed on first surface 304 and may be positioned and configured so that when LCP substrate 294 is attached to LCP outer housing 282, contact pad 296 is brought into electrical contact with electrical feedthrough 284, either directly or via an electrically conductive interface material 290. Contact pad 296 may be formed of an electrically conductive material, such as a metal or metal alloy, and in some examples, may be biocompatible. For example, contact pad 296 may include any one or more of titanium, platinum, silver, gold, alloys of titanium, platinum, silver, gold, or the like.

Electrically conductive interface material 290 may be optional, and when electrically conductive interface material 290 is used, interface material 290 may initially be applied to first end 288 of electrical feedthrough 284, as shown in FIG. 9. Instead or in addition, in examples in which electrically conductive interface material 290 is used, interface material 290 may be applied to contact pad 296. Electrically conductive interface material 290 may include an electrically conductive material, such as an electrically conductive paste, an electrically conductive epoxy, an electrically conductive reflow material, such as a solder or eutectic material, or the like.

Electrode 298 may be electrically connected to contact pad 296, e.g., via an interconnect 309 that extends through LCP substrate 298 between electrode 298 and contact pad 296. Electrode 298 may be formed of an electrically conductive material, such as a metal or metal alloy, and in some examples, may be biocompatible. For example, electrode 298 may include any one or more of titanium, platinum, silver, gold, alloys of titanium, platinum, silver, gold, or the like.

In some examples, although not shown in FIG. 9, electrode 298 may define a non-planar surface, e.g., may be shaped in three-dimensional space. For example, an outer surface 308 of electrode 298 may include curvature along at least one direction and/or may include at least one projection or depression (where the projection or depression is defined relative to a major surface of LCP substrate 294). In some examples, the non-planar surface of electrode 298 may promote tissue-electrode contact when IMD 280 is implanted in a body of a patient.

In the example illustrated in FIG. 9, LCP substrate 294 includes first protrusion 300 and second protrusion 302 (collectively "protrusions 300"). Protrusions 300 may facilitate attachment of electrode structure 292, and more particularly, LCP substrate 294, to outer surface 286 of LCP outer housing 282. In some examples, LCP substrate 294 may be attached to LCP outer housing 282 using an adhesive along protrusions 300. The adhesive may be biocompatible in some examples. In other examples, LCP substrate 294 maybe welded to LCP outer housing 282 along protrusions 300 using, for example, solvent welding, thermal welding, ultrasonic welding, laser welding, or the like. In some examples, the attachment of LCP substrate 294 to LCP outer housing 282 may form a hermetic seal between LCP substrate 294 and LCP outer housing 282, which may contribute to the hermeticity of LCP outer housing 282 by reducing a likelihood that the interface between housing 282 and electrical feedthrough 284 may provide a path for moisture ingress to within housing 282.

Although two protrusions 300 are illustrated in FIG. 9, in other examples, LCP substrate 294 may include a single protrusion or more than two protrusions 300. For example, LCP substrate 294 may include a single protrusion 302 that extends substantially continuously around contact pad 296. As another example, LCP substrate 294 may include four protrusions 300 that form a substantially continuous or discontinuous square, rectangle, oval, or circle around contact pad 296.

Additionally, in some examples, LCP substrate 294 may not include protrusions 302, and instead, first surface 304 may be substantially planar. In examples in which LCP substrate 294 does not include protrusions 302, first surface 304 may be attached to outer surface 286 of LCP outer housing 282 using an adhesive or a welding process. In some examples, LCP outer housing 282 may include protrusions to which first surface 304 of LCP substrate 294 is attaches, while in other examples, both outer surface 286 and first surface 304 may be substantially planar at the point of attachment between first surface 304 and outer surface 286.

Figure 10:
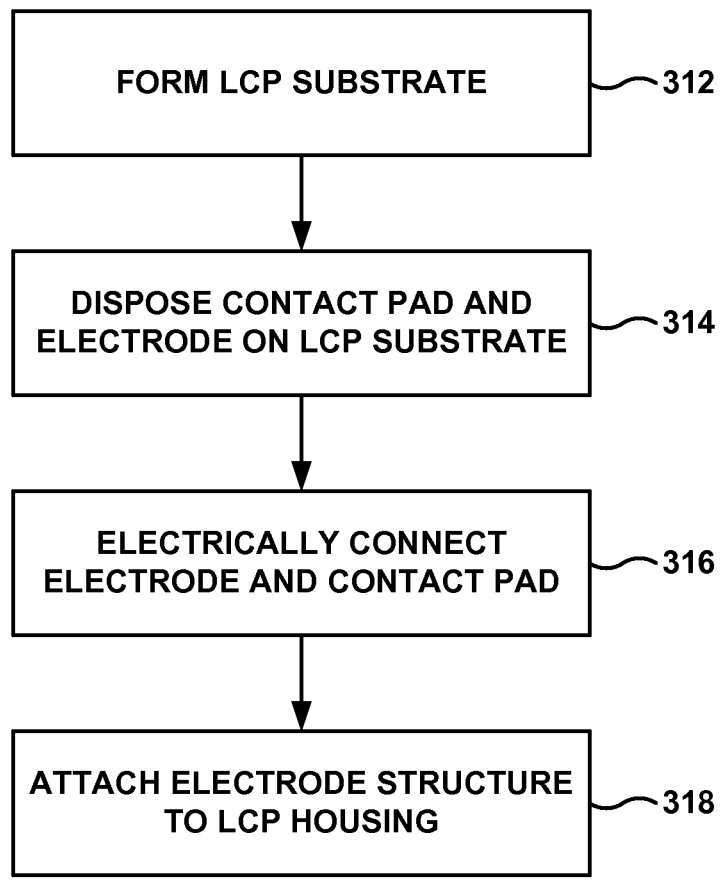
FIG. 10 is a flow diagram that illustrates an example technique that may used to form an IMD that includes the electrode structure shown in FIG. 9.

FIG. 10 is a flow diagram that illustrates an example technique that may used to form IMD 280 and electrode structure 292 shown in FIG. 9. The technique of FIG. 10 includes forming LCP substrate 294 (312). LCP substrate 292 may be formed using a variety of processes, including, for example, injection molding, compression molding, transfer molding, extrusion molding, solvent casing, or the like. In some examples, LCP substrate 292 may be formed to include protrusions 300 and/or features (e.g., depressions) shaped to receive contact pad 296 and/or electrode 298. In other examples, LCP substrate 292 may be formed to be substantially planar.

The technique of FIG. 10 also includes disposing contact pad 296 on first surface 304 of LCP substrate 294 and disposing electrode 298 on second surface 306 of LCP substrate 294 (314). Similar to electrode structure 242 shown in FIG. 5, contact pad 296 and/or electrode 298 may be disposed on LCP substrate 294 using one of a variety of processes, such as PVD, CVD, or the like. In other examples, contact pad 296 and/or electrode 298 may be disposed on LCP substrate 294 by adhering and/or soldering a pre-formed metal or alloy film first surface 304 or second surface 306, respectively.

The technique further includes electrically connecting electrode 298 and contact pad 296 (316). As described above, in some examples, electrode structure 292 may include at least one electrical interconnect 309 that extends through LCP substrate 294 between electrode 298 and contact pad 296. In some examples, electrically connecting contact pad 296 and electrode 298 (316) includes forming electrode 298 on a portion of second surface 306 that includes an exposed electrical interconnect 309 and forming contact pad 296 on a portion of first surface 304 that includes an exposed portion of the same electrical interconnect 309.

In other examples, electrically connecting contact pad 296 and electrode 298 (316) includes additional steps. For example, electrode 298 may be attached to second surface 306, e.g., using an adhesive, and then may be electrically connected to electrical interconnect 309 using a solder reflow process. Similarly, contact pad 296 may be attached to first surface 304, e.g., using an adhesive, and then may be electrically connected to electrical interconnect 309 using a solder reflow process.

Once contact pad 296 and electrode 298 have been disposed on LCP substrate 294 (314) and have been electrically connected (316), electrode structure 292 may be attached to LCP outer housing 282 (318). As described above, in some examples, attaching electrode structure 292 to LCP outer housing 282 (318) may include adhering or welding LCP substrate 294 to LCP outer housing 282. In some examples, attaching LCP substrate 294 to LCP outer housing 282 may be sufficient to bring contact pad 296 into physical contact with electrical feedthrough 284 or an optional electrically conductive interface material 290, and this may establish an electrical connection between contact pad 296 and electrical feedthrough 284. In other examples, once LCP substrate 294 is attached to LCP outer housing 282, contact pad 296 may be electrically connected to electrical feedthrough 284 via interface material 290 using a solder reflow process.

Various examples have been described. These and other examples are within the scope of the following claims.

The invention claimed is:

1. An implantable medical device (IMD) comprising:
a liquid crystal polymer (LCP) outer housing defining an outer surface of the IMD;
an electrically conductive feedthrough extending through the LCP outer housing to the outer surface; and
an electrode structure disposed on the outer surface, wherein the electrode structure comprises a LCP substrate defining a first surface and a second surface substantially opposite the first surface, a contact pad positioned on the first surface, and an electrode positioned on the second surface, and wherein the LCP substrate is attached to the LCP outer housing and the contact pad is electrically coupled to the electrically conductive feedthrough.

2. The IMD of claim 1, wherein the liquid crystal polymer (LCP) substrate is welded to the LCP outer housing, and wherein the weld forms a hermetic seal between the LCP outer housing and the LCP substrate.

3. The IMD of claim 1, wherein the contact pad is electrically coupled to the electrically conductive feedthrough through direct physical contact between the electrically conductive feedthrough and the contact pad.

4. The IMD of claim 1, wherein the contact pad is electrically coupled to the electrically conductive feedthrough via an electrically conductive interface material.

5. The IMD of claim 1, wherein the electrically conductive feedthrough defines a major axis extending between a first end and a second end electrically coupled to the contact pad, wherein the electrically conductive feedthrough comprises non-uniform width measured in a direction along a plane substantially orthogonal to the major axis.

6. The IMD of claim 5, wherein the electrically conductive feedthrough defines an electrically conductive feedthrough surface, and wherein the surface is curved in the direction of the major axis.

7. The IMD of claim 5, wherein the electrically conductive feedthrough comprises a radial projection extending radially from the major axis at a point between the first end and the second end.

8. The IMD of claim 1, further comprising circuitry, wherein the liquid crystal polymer outer housing is overmolded around the circuitry.

9. The IMD of claim 8, wherein the circuitry comprises a power source.

10. The IMD of claim 9, further comprising a printed board, wherein the circuitry is electrically connected to the printed board, and wherein the liquid crystal polymer outer housing is overmolded around the printed board and the circuitry.

11. The IMD of claim 10, wherein the printed board comprises a liquid crystal polymer.

12. The IMD of claim 10, wherein the first end of the electrically conductive feedthrough is electrically connected to an electrical trace on the printed board.

13. A method comprising:
attaching an electrode structure to an outer surface of a liquid crystal polymer (LCP) outer housing, wherein the electrode structure comprises an LCP substrate defining a first surface and a second surface substantially opposite the first surface, a contact pad disposed on the first surface, and an electrode disposed on the second surface; and
electrically connecting the contact pad to an electrically conductive feedthrough that extends through the LCP outer housing to the outer surface of the LCP outer housing.

14. The method of claim 13, further comprising forming the electrode structure comprising the liquid crystal polymer (LCP) substrate defining the first major surface and the second major surface substantially opposite the first major surface, the contact pad disposed on the first major surface, and the electrode disposed on the second major surface.

15. The method of claim 13, wherein attaching the liquid crystal polymer (LCP) substrate to the outer surface comprises welding the LCP substrate to the outer surface.

16. The method of claim 13, wherein attaching the liquid crystal polymer (LCP) substrate to the outer surface comprises adhering the LCP substrate to the outer surface.

17. The method of claim 13, wherein attaching the liquid crystal polymer (LCP) substrate to the outer surface comprises forming a hermetic seal between the LCP substrate and the outer surface.

18. The method of claim 13, wherein electrically connecting the contact pad to the electrically conductive feedthrough comprises:
applying an electrically conductive interface material to at least one of the contact pad or the electrically conductive feedthrough; and
bringing the electrically conductive feedthrough and the contact pad proximate to each other such that the electrically conductive interface material electrically couples the contact pad to the electrically conductive feedthrough.

19. The method of claim 13, further comprising:
electrically connecting a first end of the electrically conductive feedthrough to circuitry of an implantable medical device (IMD), wherein the electrically conductive feedthrough defines a major axis extending between the first end and a second end opposite the first end, and wherein the electrically conductive feedthrough comprises non-uniform width measured in a direction along a plane substantially orthogonal to the major axis; and
overmolding a liquid crystal polymer (LCP) around the circuitry and at least a portion of the electrically conductive feedthrough to form the LCP outer housing.

20. The method of claim 19, wherein electrically connecting the first end of the electrically conductive feedthrough to circuitry of the IMD comprises electrically connecting the first end of the electrically conductive feedthrough to a conductive trace of a printed board, and wherein overmolding the liquid crystal polymer (LCP) around the circuitry and at least a portion of the electrically conductive feedthrough comprises overmolding the LCP around the circuitry, the printed wire board and the at least a portion of the electrically conductive feedthrough.

* * * * *